US010669260B2

(12) United States Patent
Chan et al.

(10) Patent No.: US 10,669,260 B2
(45) Date of Patent: *Jun. 2, 2020

(54) COMPOUNDS TARGETING PROTEINS, COMPOSITIONS, METHODS, AND USES THEREOF

(71) Applicant: BioTheryX, Inc., Chappaqua, NY (US)

(72) Inventors: Kyle W. H. Chan, San Diego, CA (US); Leah Fung, San Diego, CA (US); Robert Sullivan, Vista, CA (US); Paul E. Erdman, San Diego, CA (US); Frank Mercurio, Rancho Santa Fe, CA (US)

(73) Assignee: BioTheryX, Inc., Chappaqua, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/801,124

(22) Filed: Nov. 1, 2017

(65) Prior Publication Data

US 2018/0065952 A1 Mar. 8, 2018

Related U.S. Application Data

(62) Division of application No. 15/158,340, filed on May 18, 2016, now Pat. No. 9,822,098.

(60) Provisional application No. 62/165,469, filed on May 22, 2015.

(51) Int. Cl.
| | |
|---|---|
| *A61K 31/454* | (2006.01) |
| *A61K 31/55* | (2006.01) |
| *A61K 45/06* | (2006.01) |
| *C07D 403/04* | (2006.01) |
| *C07D 401/04* | (2006.01) |

(52) U.S. Cl.
CPC .......... *C07D 403/04* (2013.01); *A61K 31/454* (2013.01); *A61K 31/55* (2013.01); *A61K 45/06* (2013.01); *C07D 401/04* (2013.01)

(58) Field of Classification Search
CPC ....... A61K 31/454; A61K 31/55; A61K 45/06
See application file for complete search history.

(56) References Cited

U.S. PATENT DOCUMENTS

| 5,552,397 A | 9/1996 | Karanewsky et al. |
| 7,968,708 B2 | 6/2011 | Hangauer et al. |
| 9,822,098 B2 | 11/2017 | Chan et al. |
| 9,938,302 B2 | 4/2018 | Chan et al. |
| 10,144,745 B2 | 12/2018 | Chan et al. |
| 2018/0230167 A1 | 8/2018 | Chan et al. |

FOREIGN PATENT DOCUMENTS

| CN | 104004122 | 8/2014 |
| JP | 2001-503384 | 3/2001 |
| JP | 2002-506861 | 3/2002 |
| WO | WO 97/38705 | 10/1997 |
| WO | WO 98/03502 | 1/1998 |
| WO | WO 99/47512 | 9/1999 |
| WO | WO 08/070161 | 6/2008 |
| WO | WO 14/089495 | 6/2014 |
| WO | WO 16/191178 | 12/2016 |
| WO | WO 17/197055 | 11/2017 |
| WO | WO 17/197056 | 11/2017 |

OTHER PUBLICATIONS

Bell et al., 2015, Sustained in vivo signaling by long-lived IL-2 induces prolonged increases of regulatory T cells, Journal of Autoimmunity, 56:66-80.
Belyaev et al., May 1991, A novel synthetic route to $N^6$-methyl-L-lysine and $N^5$-methyl-L-ornithine via $N^3$-protected (S)-3-aminolactams, Synthesis, 417-419.
Belyaev, Jan. 16, 1995, A novel synthetic route to enantiomers of epsilon-hydroxynorleucine and epsilon-chloronorleucine from L- and D,L-lysine, Tetrahedron Letters, 36(3):439-440.
Billot et al., Feb. 10, 2011, Deregulation of aiolos expression in chronic lymphocytic leukemia is associated with epigenetic modifications, Blood, 117(6):1917-1927.
Cary, 1992, 8.15 Sulfonate esters as substrates in nucleophilic substitution reactions, in Organic Chemistry Second Edition, McGraw-Hill, Inc., New York, pp. 328-331.
Desagher et al., Sep. 2001, Phosphorylation of bid by casein kinases I and II regulates its cleavage by caspase 8, Molecular Cell, 8:601-611.
Eger et al., 1990, Synthesis, central nervous system activity and teratogenicity of a homothalidomide, Arzneimittel-Forschung, 40(10)1073-1075.
Greene et al., eds., Protective Groups in Organic Synthesis, John Wiley & Sons, Inc., New York, 1999.
IUPAC-IUB Commission on Biochemical Nomenclature, Abbreviated Nomenclature of Synthetic {olypeptides (Polymerized Amino Acids) Revised Recommendations (1971), Biochemistry, 11(5):942-944, 1972.
Kikuchi et al., 2009, Lacking of aiolos accelerates pre-mature B cell apoptosis mediated by BCR signaling through elevation in cytochrome c release, Biochimica et Biophysica Acta, 1793:1304-1314.

(Continued)

*Primary Examiner* — Bruck Kifle
(74) *Attorney, Agent, or Firm* — Knobbe, Martens, Olson & Bear, LLP

(57) ABSTRACT

The present invention provides modulators of protein function, to restore protein homeostasis, including cytokine, aiolos, and/or ikaros activity, and cell-cell adhesion. The invention provides methods of modulating protein-mediated diseases, such as cytokine-mediated diseases, disorders, conditions, or responses. Compositions, including in combination with other cytokine and inflammatory mediators, are provided. Methods of treatment, amelioration, or prevention of protein-mediated diseases, disorders, and conditions, such as cytokine-mediated diseases, disorders, and conditions, including inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, and cancer, are provided.

15 Claims, 18 Drawing Sheets

(56) References Cited

OTHER PUBLICATIONS

Knippschild et al., 2005, The casein kinase 1 family: participation in multiple cellular processes in eukaryotes, Cellular Signalling 17:675-689.
Lee et al., Jun. 2011, Assessing chiral self-recognition using chiral stationary phases, Tetrahedron, 67:7143-7147.
Li et al., May 12, 2014, Aiolos promotes anchorage independence by silencing p66$^{Sch}$ transcription in cancer cells, Cancer Cell, 25:575-589.
McMurray, 2000, Organic Chemistry Fifth Edition, Brooks/Cole, Pacific Grove, CA, pp. 398, 408.
McOmie ed., Protective Groups in Organic Chemistry, Plenum Press, London and New York, 1973.
Ouellet et al., 2013, Regulation of host gene expression by HIV-1 TAR microRNAs, Retrovirology, 10:86.
Robl et al., 1994, A synthetic route for the generation of C-7 substituted azepinones, Tetrahedron Letters, 35(9):1393-1396.
Robl et al., 1994, Peptidomimetic synthesis: a novel, highly stereoselective route to substituted Freidinger lactams, J. Am. Chem. Soc., 116(6):2348-2355.
Robl et al., 1996, Dual metalloprotease inhibitors. 6. Incorporation of bicyclic and substituted monocyclic azepinones as dipeptide surrogates in angiotensin-converting enzyme/neutral endopeptidase inhibitors, J. Med. Chem. 39:494-502.
Rosenberg et al., Apr. 3, 2015, Adoptive cell transfer as personalized immunotherapy for human cancer, 348(6230):62-68.
Skrombolas et al., Feb. 2014, Challenges and developing solutions for increasing the benefits of IL-2 treatment in tumor therapy, Expert Rev Clin Immunol., 19(2):207-217.
Streitwieser et al., 1981, 8.10 Leaving Groups, in Introduction to Organic Chemistry Second Edition, Macmillan Publishing Co., Inc., New York, pp. 169-171.
International Search Report and Written Opinion dated Aug. 4, 2016 in PCT/US2016/033133.
Belyaev et al., 1992, A novel synthetic route to L-α-aminoadipic acid, Izsvestiya Akademi Nauk, Seriya Khimicheskaya, 7:1692-1693.
Audit, 1994, Thalidomide-induced polymine acylation: a new insight into the acylation mechanism, Biogenic Amines, 10(6):543-554.
International Search Report and Written Opinion dated Jul. 28, 2017 in PCT/US2017/032936.
Lai et al., 2016, Modular PROTEC design for the degradation of oncogenic BCR-ABL, Angewandte Chemie International Edition, 55(2):807-810.
Ruchelman et al., 2013, Isosteric analogs of lenalidomide and pomlidomide: synthesis and biological activity, Bioorganic & Medicinal Chemistry Letters, 23(1):360-365.
CAS RN 131926-36-8, STN entry date Feb. 9, 1991, 1H-Isoindole-1,3(2H)-dione, 2-(hexahydro-2,7-dioxo-1H-azepin-3-yl)-, (S)-.
CAS RN 131926-37-9, STN entry date Feb. 9, 1991, 1H-Isoindole-1,3(2H)-dione, 2-(hexahydro-2,7-dioxo-1H-azepin-3-yl)-, (R)-.
Chang et al., 2013, Mechanism of immunomodulatory drugs' action in the treatment of multiple myeloma, Acta Biochim Biophys Sin, 46(3):240-253.
Kobayashi, 2014, How the anti-tumor effect of Lenalidomide, thalidomide derivative, is expressed, Farumashia, 2014, 50(11):1145.
Torigoe et al., 2016, Pomalidomide (Pomalyst capsule 1 mg/2 mg/3 mg/4 mg): pharmacokinetics, pharmacodynamics and clinical study outcome, Japanese Journal of Pharmacology, 148(3):154-161.
Winter et al., 2015, Selective target protein degradation via phthalimide conjugation, Science, 348(6241):1376.

US 10,669,260 B2

COMPOUNDS TARGETING PROTEINS, COMPOSITIONS, METHODS, AND USES THEREOF

CROSS-REFERENCE TO RELATED APPLICATIONS

This application is a divisional of U.S. patent application Ser. No. 15/158,340, filed May 18, 2016, which claims the benefit of U.S. Provisional Patent Application No. 62/165,469, filed May 22, 2015; all of which is expressly incorporated by reference its entirety. Any and all applications for which a foreign or domestic priority claim is identified in the Application Data Sheet as filed with the present application are hereby incorporated by reference under 37 CFR 1.57.

BACKGROUND OF THE INVENTION

Field of the Invention

Compounds, methods of making such compounds, pharmaceutical compositions and medicaments comprising such compounds, and methods of using such compounds to treat, prevent or diagnose diseases, disorders, or conditions associated with protein malfunction are provided.

Description of the Related Technology

Aberrant protein function, and/or protein imbalance is a hallmark of many disease states. For example, the functioning of the immune system is finely balanced by the activities of pro-inflammatory and anti-inflammatory mediators or cytokines. Some cytokines promote inflammation (pro-inflammatory cytokines), whereas other cytokines suppress the activity of the pro-inflammatory cytokines (anti-inflammatory cytokines). For example, IL-4, IL-10, and IL-13 are potent activators of B lymphocytes, and also act as anti-inflammatory agents. They are anti-inflammatory cytokines by virtue of their ability to suppress genes for pro-inflammatory cytokines such as IL-1, TNF, and chemokines.

Unregulated activities of these mediators can lead to the development of serious inflammatory conditions. For example, autoimmune diseases arise when immune system cells (lymphocytes, macrophages) become sensitized against the "self" Lymphocytes, as well as macrophages, are usually under control in this system. However, a misdirection of the system toward the body's own tissues may happen in response to still unexplained triggers. One hypothesis is that lymphocytes recognize an antigen which mimics the "self" and a cascade of activation of different components of the immune system takes place, ultimately leading to tissue destruction. Genetic predisposition has also been postulated to be responsible for autoimmune disorders.

Tumor necrosis factor-alpha (TNF-alpha) and interleukin-1 (IL-I) are pro-inflammatory cytokines that mediate inflammatory responses associated with infectious agents and other cellular stresses. Overproduction of these cytokines is believed to underlie the progression of many inflammatory diseases including rheumatoid arthritis (RA), Crohn's disease, inflammatory bowel disease, multiple sclerosis, endotoxin shock, osteoporosis, Alzheimer's disease, congestive heart failure, and psoriasis among others.

Recent data from clinical trials support the use of protein antagonists of cytokines, for example soluble TNF-alpha receptor fusion protein (etanercept) or the monoclonal TNF-alpha antibody (infliximab), for the treatment of rheumatoid arthritis, Crohn's disease, juvenile chronic arthritis and psoriatic arthritis. Thus, the reduction of pro-inflammatory cytokines such as TNF-alpha and interleukin-1 (IL-1) has become an accepted therapeutic approach for potential drug intervention in these conditions.

Moreover, IL-2 is now FDA approved for the treatment of renal cancer and melanoma patients, with durable, complete remissions achieved with IL-2 up to 148 months. However, the short half-life of IL-2 in serum requires that large amounts of IL-2 be injected to achieve therapeutic levels. Many attempts have been made to minimize side effects of systemic IL-2 treatment, for example, introducing IL-2 directly into the tumor, though this complicates treatment, and has largely been unsuccessful.

Local delivery of cytokines is appealing compared to systemic delivery for a variety of reasons. It takes advantage of the natural biology of cytokines that have evolved to act locally in a paracrine or autocrine fashion. Local expression also dramatically minimizes many of the side effects of systemic delivery of cytokines. Thus, compounds and methods to increase local expression of IL-2 would be better tolerated than high dose IL-2 treatment, which would expand therapeutic utility of strategies that increase IL-2. However, increasing IL-2 levels substantially beyond normal physiologic concentrations can lead to serious side-effects, such as autoimmune disease. Accordingly, restoration and maintenance of IL-2 homeostasis is critical for addressing IL-2 mediated disorders.

Additional targets include several candidate genes involved in apoptosis and cell survival, including the zinc-finger transcription factor Aiolos. Aiolos is a transcription factor whose expression is restricted to lymphoid lineages. Aiolos binds to the Bcl-2 promoter, and also interacts with the Bcl-2 and Bcl-XL proteins to promote cell survival. Upregulation of Aiolos expression, for example, can reduce apoptosis of HIV-1 infected cells.

Likewise, expression of Aiolos in lung and breast cancers predicts significantly reduced patient survival. Aiolos decreases expression of a large set of adhesion-related genes, disrupting cell-cell and cell-matrix interactions, facilitating metastasis. Aiolos may also function as an epigenetic driver of lymphocyte mimicry in certain metastatic epithelial cancers. Thus, down-regulation of Aiolos may reduce or eliminate metastasis.

Similarly, the casein kinase 1 family of proteins plays a role in the mitotic spindle formation, in DNA repair, and in RNA metabolism. See, e.g., Knippschild, et al., *Cell Signal*, Vol 17, pp. 675-689 (2005). There are six isoforms in humans: $\alpha$, $\gamma1$, $\gamma2$, $\gamma3$, $\delta$ and $\epsilon$. CK1$\alpha$ has been shown to have an anti-apoptotic function; its inhibition increased Fas-induced apoptosis, whereas the overexpression of CK1$\alpha$ delayed BID-mediated cell death. See, e.g., Desagher, et al., *Mol Cell.*, Vol. 8, pp. 601-611 (2001). In addition, CK1$\alpha$ inhibits TRAIL induced apoptosis by modification of the TNF receptor or FADD at the death-inducing signaling complex (DISC). Thus, downregulation of CK1$\alpha$ leads to enhancement of TRAIL-induced cell death. CK1$\alpha$ also promotes cell survival by interacting with the retinoid X receptor (RXR). Downregulation of CK1$\alpha$ enhances the apoptotic effect of RXR agonists. Likewise, the ikaros family of proteins are tumor suppressors that play a role in leukemia.

In some instances, a protein malfunction is not a direct result of protein over- or under-expression, or alterations to the protein's sequence and structure. Rather, the malfunction may simply be the inability of a wild-type protein, with normal function and expression levels, to (for example) combat a growing tumor. Ikaros, for example, functions as transcriptional repressor of IL-2. Thus, degradation of ikaros induces expression of IL-2, which in turn serves to boost the immune response and anti-cancer function.

Accordingly, compounds that modulate protein function in both normal proteins and directly malfunctioning proteins, and restore protein homeostasis are necessary for the treatment and prevention of disease.

SUMMARY OF THE INVENTION

The compounds disclosed in the present application have been discovered to exert surprising and unexpected biological effects. In particular, the compounds disclosed in the present application modulate protein levels to restore protein homeostasis.

Some embodiments provide a compound of Formula (I):

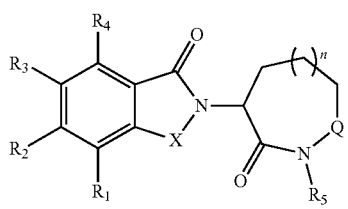

(I)

or a pharmaceutically acceptable salt or solvate thereof.

In some embodiments, $R_1$, $R_2$, $R_3$, and $R_4$, are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl;

In some embodiments, $R_5$ is selected from the group consisting of H, deuterium, oxo, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, X is selected from the group consisting of $C(R_5)_2$, $CH(R_5)$, $CH_2$, C=O, and C=S.

In some embodiments, Q is selected from the group consisting of $C(R_5)_2$, $CH(R_5)$, $CH_2$, C=O, C=S, S=O, and $SO_2$.

In some embodiments, n is 1 or 2.

In some embodiments, Q is selected from the group consisting of $CH_2$ and C=O. In some embodiments, Q is $CH_2$. In some embodiments, Q is C=O.

In some embodiments, n is 1. In some embodiments, n is 2.

In some embodiments, $R_5$ is H.

In some embodiments, $R_5$ is optionally substituted $C_1$ to $C_6$ alkyl. In some embodiments, $R_5$ is optionally substituted $C_6$ to $C_{10}$ aryl.

In some embodiments, X is $CH_2$. In some embodiments, X is C=O. In some embodiments, $R_1$ is $NH_2$. In some embodiments, $R_1$ is $NO_2$. In some embodiments, $R_2$ is $NH_2$. In some embodiments, $R_2$ is $NO_2$. In some embodiments, $R_1$ is $CH_3$. In some embodiments, $R_1$ is chloro. In some embodiments, $R_1$ is methoxy.

In some embodiments, the compound of Formula (I) is present in a form of a racemic mixture. In some embodiments, the compound of Formula (I) has an S-configuration. In some embodiments, the compound of Formula (I) has an R-configuration.

In some embodiments, the compound of Formula (I) is selected from the group consisting of:

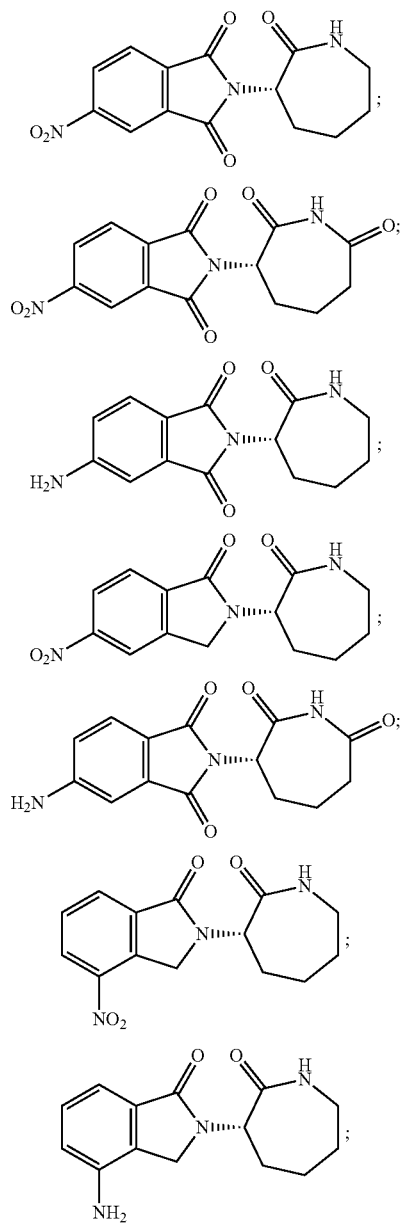

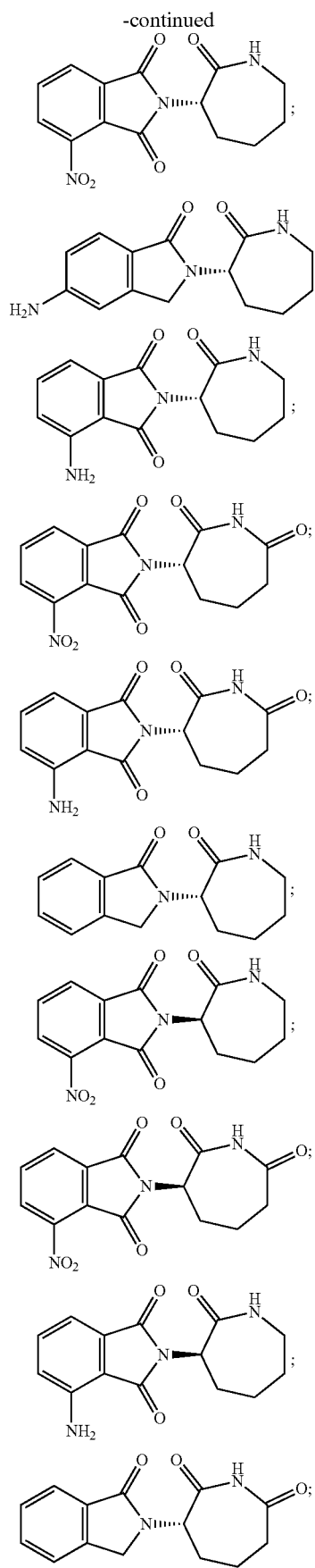
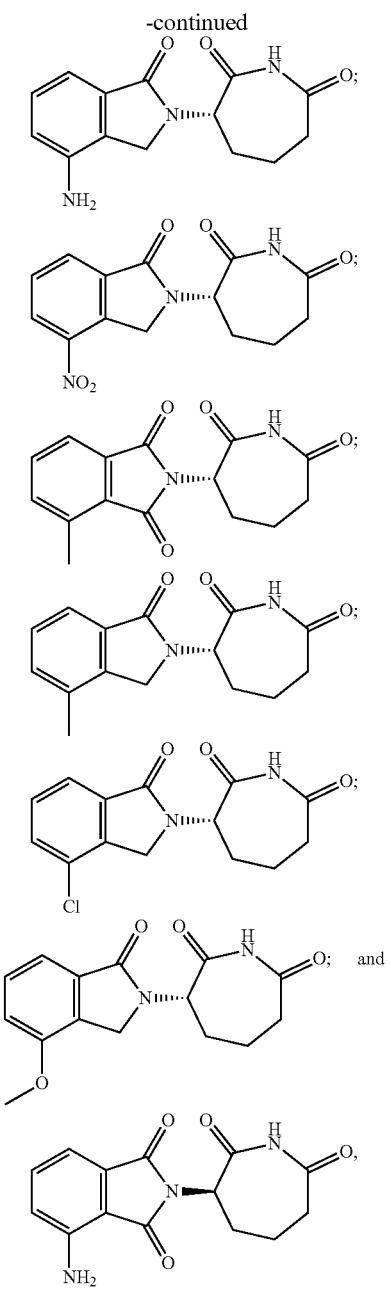
or pharmaceutically acceptable salts, solvates, and combinations of the foregoing. Preferred embodiments include any one of the above compounds, or combinations thereof.
Some embodiments provide a pharmaceutical composition comprising a compound of Formula (I):
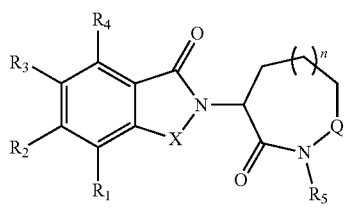

or a pharmaceutically acceptable salt or solvate thereof, and at least one pharmaceutically acceptable carrier.

In some embodiments, $R_1$, $R_2$, $R_3$, and $R_4$, are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, $R_5$ is selected from the group consisting of H, deuterium, oxo, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, X is selected from the group consisting of $C(R_5)_2$, $CH(R_5)$, $CH_2$, C=O, and C=S.

In some embodiments, Q is selected from the group consisting of $C(R_5)_2$, $CH(R_5)$, $CH_2$, C=O, C=S; S=O, and $SO_2$.

In some embodiments, Q is selected from the group consisting of $CH_2$ and C=O. In some embodiments, Q is $CH_2$. In some embodiments, Q is C=O.

In some embodiments, n is 1. In some embodiments, n is 2.

In some embodiments, $R_5$ is H. In some embodiments, $R_5$ is optionally substituted $C_1$ to $C_6$ alkyl. In some embodiments, $R_5$ is optionally substituted $C_6$ to $C_{10}$ aryl.

In some embodiments, X is $CH_2$. In some embodiments, X is C=O. In some embodiments, $R_1$ is $NH_2$. In some embodiments, $R_1$ is $NO_2$. In some embodiments, $R_2$ is $NH_2$. In some embodiments, $R_2$ is $NO_2$. In some embodiments, $R_1$ is $CH_3$. In some embodiments, $R_1$ is chloro. In some embodiments, $R_1$ is methoxy.

In some embodiments, the pharmaceutical composition of Formula (I) is in a form of a racemic mixture. In some embodiments, the pharmaceutical composition of Formula (I) has an S-configuration. In some embodiments, the pharmaceutical composition of Formula (I) has an R-configuration.

In some embodiments, the compound of Formula (I) is selected from the group consisting of:

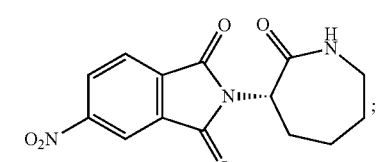

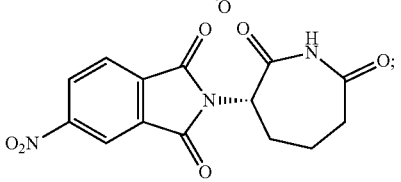

-continued

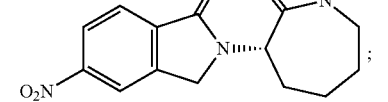

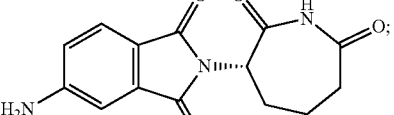

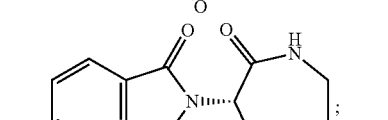

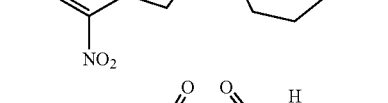

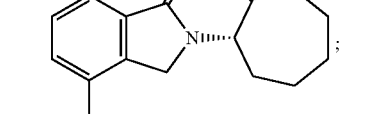

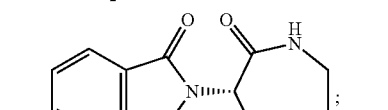

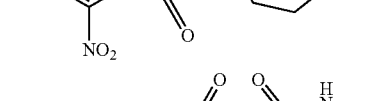

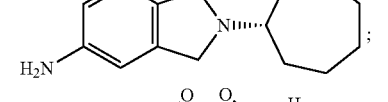

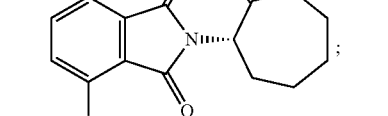

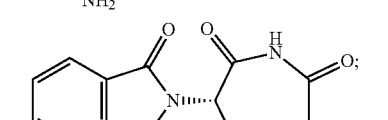

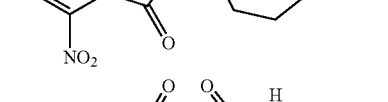

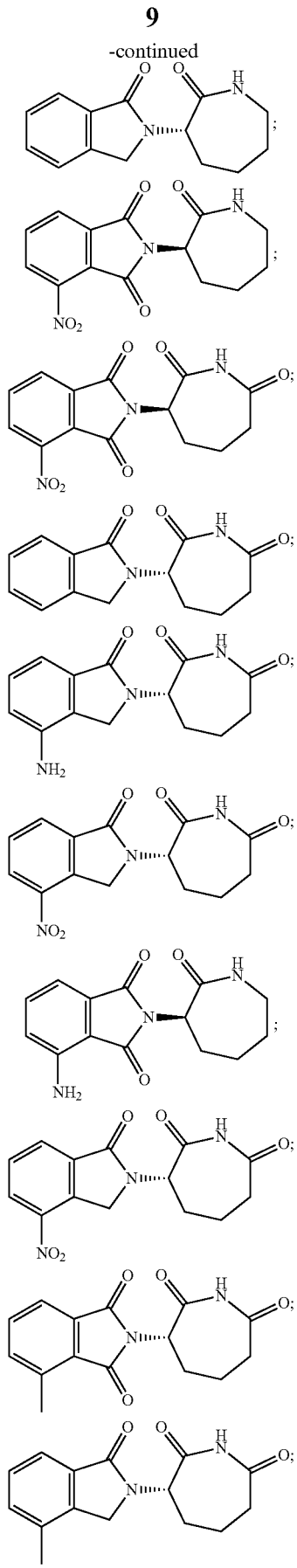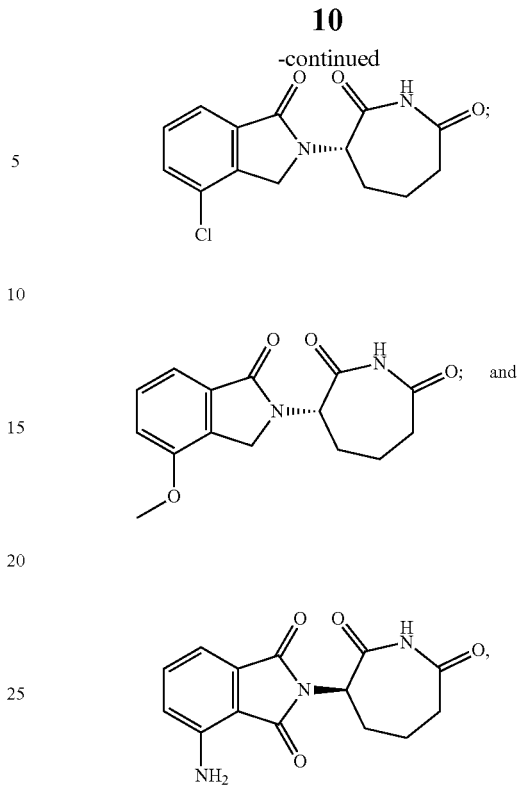

or pharmaceutically acceptable salts, solvates, and combinations of the foregoing.

In some embodiments, the composition is formulated for oral, parenteral, topical, ophthalmic, inhalation, nasal, or intravenous administration.

In some embodiments, the pharmaceutical composition further comprises a second therapeutic agent. In some embodiments, the second therapeutic agent is selected from the group consisting of anti-inflammatory agents, anti-cancer agents, immunostimulatory agents, and immunosuppressive agents. In some embodiments, the second therapeutic agent is an anti-cancer agent.

Some embodiments provide methods of treating, ameliorating, or preventing a disease, disorder, or condition associated with protein function or imbalance, comprising administering a therapeutically effective amount of a compound of Formula (I):

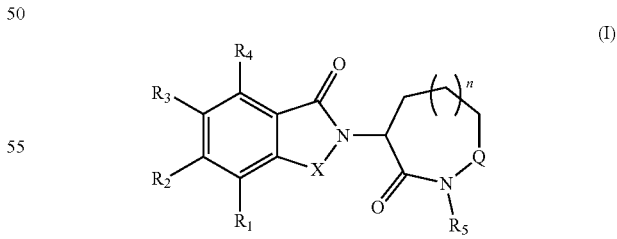

or a pharmaceutically acceptable salt or solvate thereof, to a subject in need thereof.

Some embodiments provide methods of treating, ameliorating, or preventing a disease, disorder, or condition associated with protein malfunction, comprising administering a therapeutically effective amount of a compound of Formula (I):

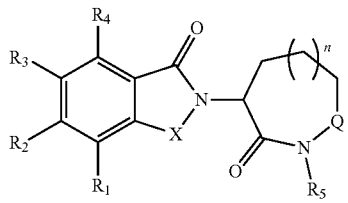

or a pharmaceutically acceptable salt or solvate thereof, to a subject in need thereof.

In some embodiments, protein malfunction is due to overexpression of said protein. In some embodiments, protein malfunction is due to increased activity of said protein. In some embodiments, protein malfunction is due to decreased degradation of said protein. In some embodiments, protein malfunction is due to misregulation of a signaling cascade associated with said protein Some embodiments provide methods of restoring protein homeostatis, comprising administering a therapeutically effective amount of a compound of Formula (I):

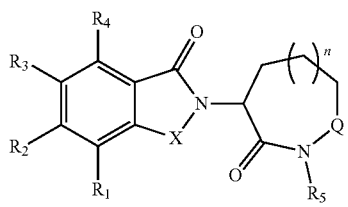

or a pharmaceutically acceptable salt or solvate thereof, to a subject in need thereof. In some embodiments, the protein imbalance is associated with a protein selected from cytokines, aiolos, ikaros, and/or one or more cell-cell adhesion proteins. In some embodiments, the protein imbalance is associated with cancer. In some embodiments, the subject in need thereof is known to possess a protein imbalance. In some embodiments, the subject in need thereof is known to possess a protein imbalance in one or more of cytokines, aiolos, ikaros, and/or one or more cell-cell adhesion proteins. In some embodiments, the subject in need thereof is known to possess wild-type p53.

In some embodiments, $R_1$, $R_2$, $R_3$, and $R_4$, are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, $R_5$ is selected from the group consisting of H, deuterium, oxo, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, X is selected from the group consisting of $C(R_5)_2$, $CH(R_5)$, $CH_2$, C=O, and C=S.

In some embodiments, Q is selected from the group consisting of $C(R_5)_2$, $CH(R_5)$, $CH_2$, C=O, C=S; S=O, and $SO_2$.

In some embodiments, n is 1 or 2.

In some embodiments, the disease, disorder, or condition is selected from the group consisting of inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, and cancer.

In some embodiments, the compound of Formula (I) is administered in combination with a second therapeutic agent. In some embodiments, the second therapeutic agent is selected from the group consisting of anti-inflammatory agents, anti-cancer agents, immunostimulatory agents, and immunosuppressive agents. In some embodiments, the second therapeutic agent is an anti-cancer agent.

In some embodiments, Q is selected from the group consisting of $CH_2$ and C=O. In some embodiments, Q is $CH_2$. In some embodiments, Q is C=O.

In some embodiments, n is 1. In some embodiments, n is 2.

In some embodiments, $R_5$ is H. In some embodiments, $R_5$ is optionally substituted $C_1$ to $C_6$ alkyl. In some embodiments, $R_5$ is optionally substituted $C_6$ to $C_{10}$ aryl.

In some embodiments, X is $CH_2$. In some embodiments, X is C=O.

In some embodiments, $R_1$ is $NH_2$. In some embodiments, $R_1$ is $NO_2$. In some embodiments, $R_2$ is $NH_2$. In some embodiments, $R_2$ is $NO_2$. In some embodiments, $R_1$ is $CH_3$. In some embodiments, $R_1$ is chloro. In some embodiments, $R_1$ is methoxy.

In some embodiments, the compound of Formula (I) is in a form of a racemic mixture. In some embodiments, the compound of Formula (I) has an S-configuration. In some embodiments, the compound of Formula (I) has an R-configuration.

In some embodiments, the compound of Formula (I) is selected from the group consisting of:

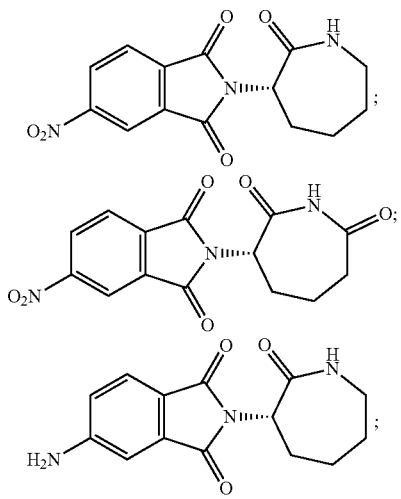

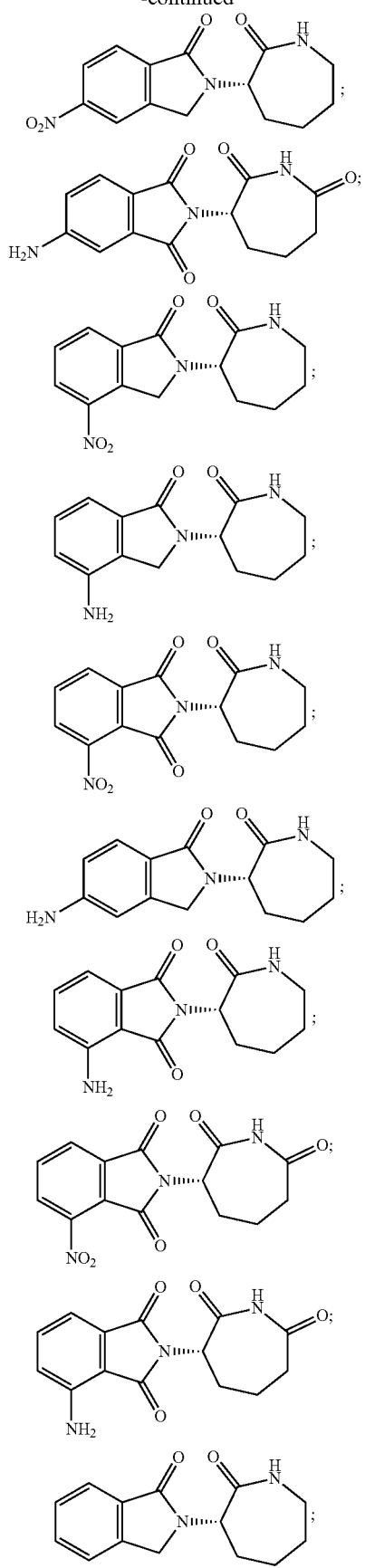
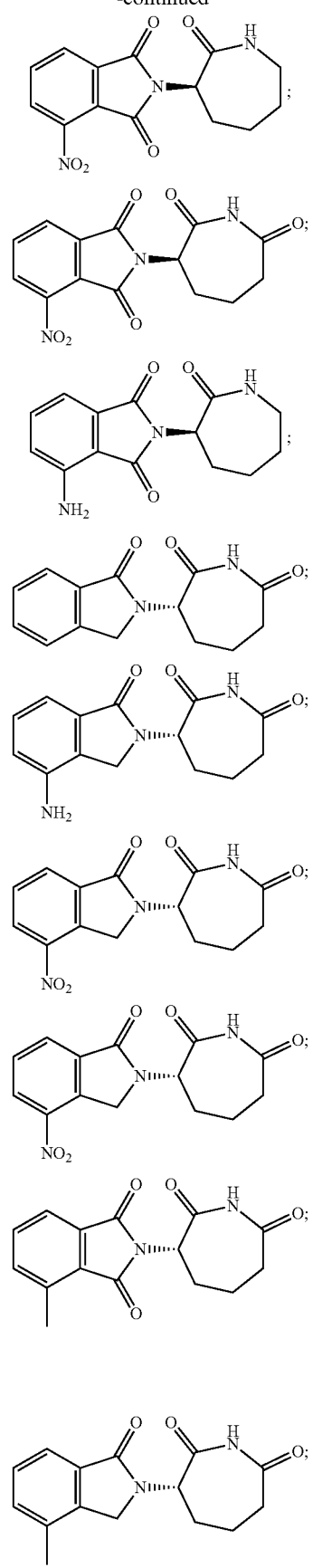

-continued

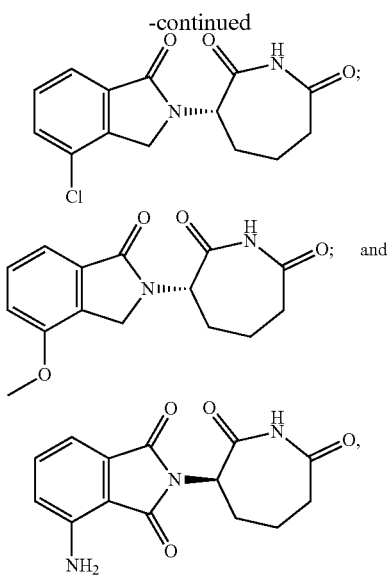

a pharmaceutically acceptable salts, solvates, and combinations of the foregoing.

Some embodiments provide methods of inhibiting the activity of a protein or proteins, for example, cytokine activity, aiolos activity, and/or ikaros activity, comprising contacting a cell with a compound of Formula (I):

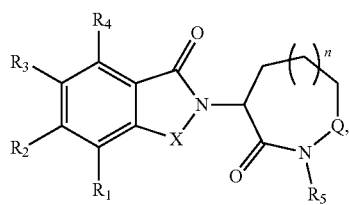

or a pharmaceutically acceptable salt or solvate thereof.

Some embodiments provide methods of modulating cell-cell adhesion, comprising contacting a cell with a compound of Formula (I):

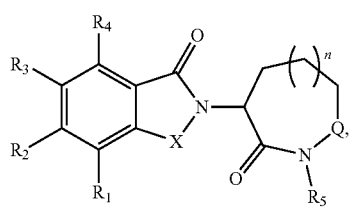

or a pharmaceutically acceptable salt or solvate thereof.

In some embodiments, $R_1$, $R_2$, $R_3$, and $R_4$, are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl;

$R_5$ is selected from the group consisting of H, deuterium, oxo, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, X is selected from the group consisting of $C(R_5)_2$, $CH(R_5)$, $CH_2$, C=O, and C=S.

In some embodiments, Q is selected from the group consisting of $C(R_5)_2$, $CH(R_5)$, $CH_2$, C=O, C=S; S=O, and $SO_2$.

In some embodiments, n is 1 or 2.

In some embodiments, Q is selected from the group consisting of $CH_2$ and C=O. In some embodiments, Q is $CH_2$. In some embodiments, Q is C=O.

In some embodiments, n is 1. In some embodiments, n is 2.

In some embodiments, $R_5$ is H. In some embodiments, $R_5$ is optionally substituted $C_1$ to $C_6$ alkyl. In some embodiments, $R_5$ is optionally substituted $C_6$ to $C_{10}$ aryl.

In some embodiments, X is $CH_2$. In some embodiments, X is C=O.

In some embodiments, $R_1$ is $NH_2$. In some embodiments, $R_1$ is $NO_2$. In some embodiments, $R_2$ is $NH_2$. In some embodiments, $R_2$ is $NO_2$. In some embodiments, $R_1$ is $CH_3$. In some embodiments, $R_1$ is chloro. In some embodiments, $R_1$ is methoxy.

In some embodiments, the compound of Formula (I) is in a form of a racemic mixture. In some embodiments, the compound of Formula (I) has an S-configuration. In some embodiments, the compound of Formula (I) has an R-configuration.

In some embodiments, the compound of Formula (I) is selected from the group consisting of:

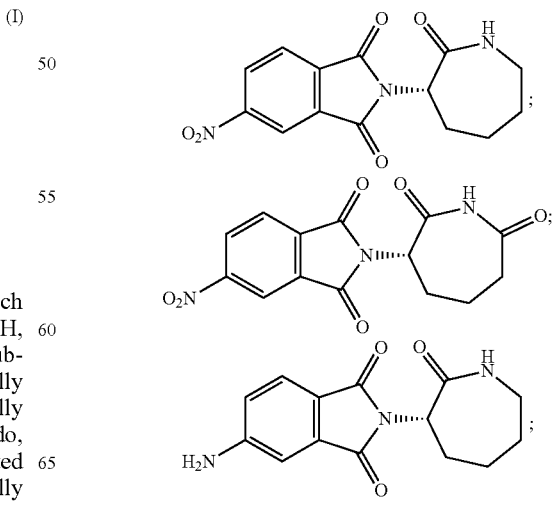

-continued
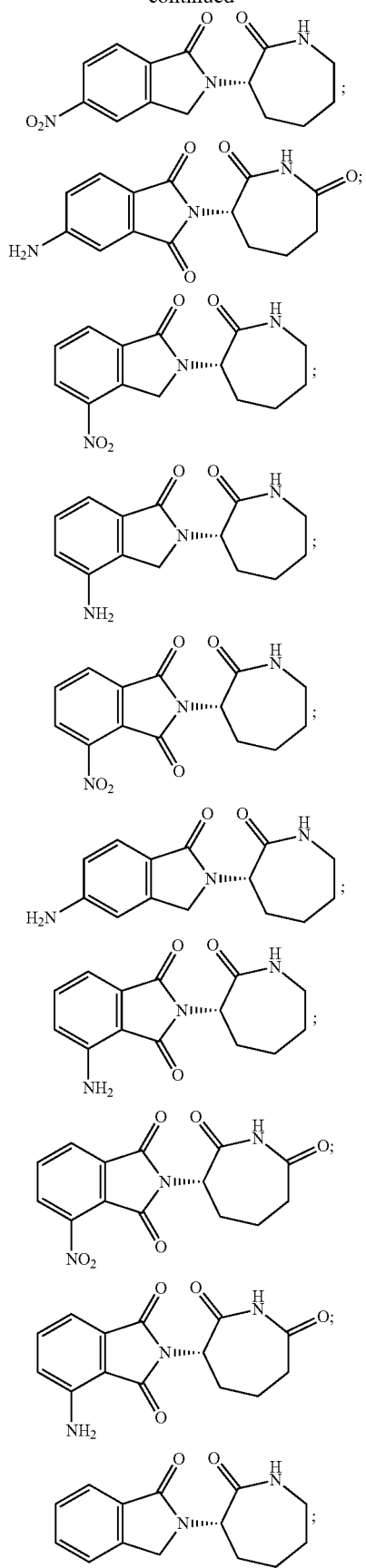
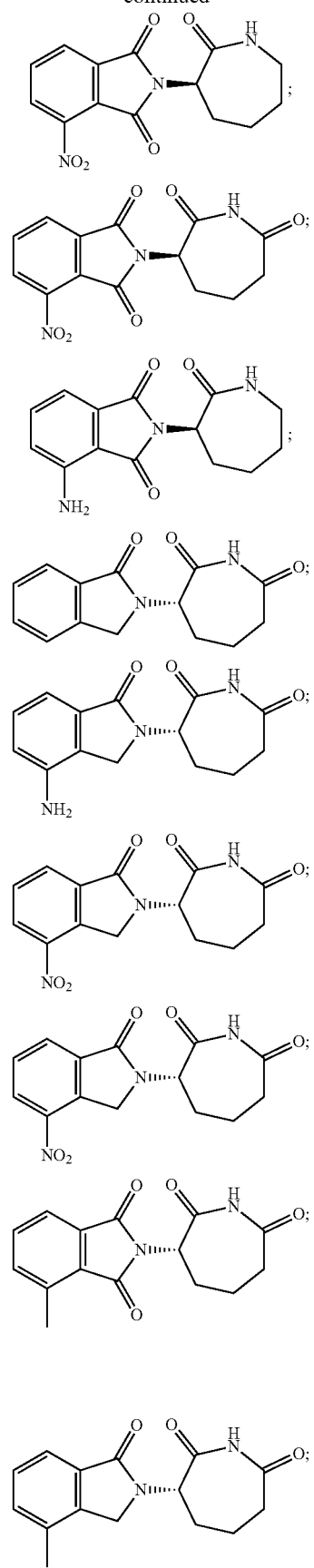

-continued

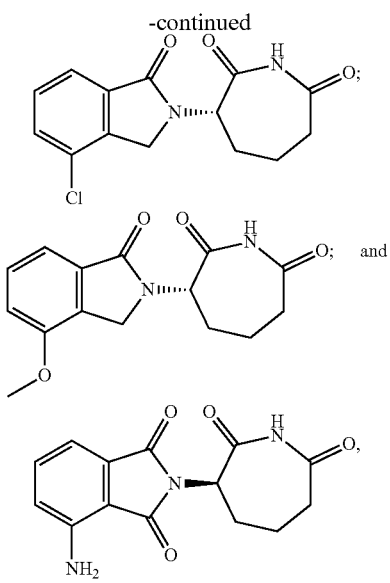

a pharmaceutically acceptable salts, solvates, and combinations of the foregoing.

In some embodiments, the compound of Formula (I) is provided in combination with a second agent. In some embodiments, the second agent is selected from the group consisting of anti-inflammatory agents, anti-cancer agents, immunostimulatory agents, and immunosuppressive agents. In some embodiments, the second agent is an anti-cancer agent.

Any of the features of an embodiment is applicable to all embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other embodiments. Any embodiment of a method can comprise another embodiment of a compound, and any embodiment of a compound can be configured to perform a method of another embodiment.

DETAILED DESCRIPTION

Figure 1:
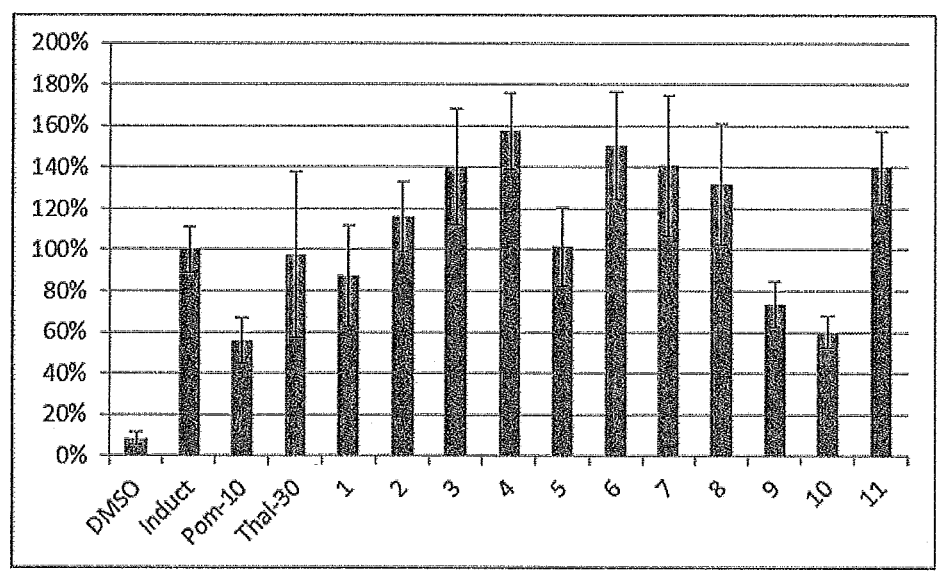
FIG. 1 represents the activity against M-1-beta in CD14 macrophages, plated in 96 well plates and treated with 100 ng/mL macrophage colony-stimulating factor (M-CSF) for up to 1 week to differentiate cells into macrophages. Cells were pretreated with compounds for 1 hour and then induced with either 200 ng/ml LPS or 20 ng/ml of TNF-alpha for 18-24 hours. Cytokines in the media were measured according to MesoScale protocol. Pom-10 is 10 uM pomalidomide; Thal-30 is 30 uM thalidomide. The negative control wells were treated with DMSO. Cells were treated with the indicated compound (20 uM). Compound activity is measured as a percentage of LPS-induced activity.

Some embodiments provide a compound of Formula (I):

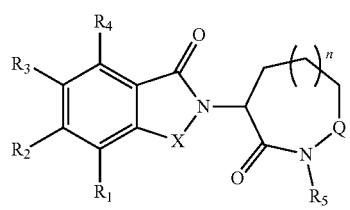

(I)

Some embodiments provide a pharmaceutically acceptable salt or solvate of a compound of Formula (I).

$R_1$, $R_2$, $R_3$, and $R_4$, are each independently selected from H, deuterium, hydroxyl, halogen, cyano, nitro, optionally substituted amino, optionally substituted amido, optionally substituted ester, optionally substituted sulfonyl, optionally substituted S-sulfonamido, optionally substituted N-sulfonamido, optionally substituted sulfonate, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, $R_2$, $R_3$, and $R_4$, are each H. In some embodiments, $R_1$, $R_3$, and $R_4$, are each H. In some embodiments, $R_1$, $R_2$, and $R_4$, are each H. In some embodiments, $R_1$, $R_2$, and $R_3$, are each H. In some embodiments, none of $R_1$, $R_2$, $R_3$, and $R_4$, are H.

In some embodiments, $R_2$, $R_3$, and $R_4$, are each deuterium. In some embodiments, $R_1$, $R_3$, and $R_4$, are each deuterium. In some embodiments, $R_1$, $R_2$, and $R_4$, are each deuterium. In some embodiments, $R_1$, $R_2$, and $R_3$, are each deuterium. In some embodiments, none of $R_1$, $R_2$, $R_3$, and $R_4$, are deuterium.

In some embodiments, $R_2$, $R_3$, and $R_4$, are each halogen. In some embodiments, $R_1$, $R_3$, and $R_4$, are each halogen. In some embodiments, $R_1$, $R_2$, and $R_4$, are each halogen. In some embodiments, $R_1$, $R_2$, and $R_3$, are each halogen. In some embodiments, none of $R_1$, $R_2$, $R_3$, and $R_4$, are halogen.

In some embodiments, $R_1$ is optionally substituted amino. In some embodiments, $R_1$ is unsubstituted amino. In some embodiments, $R_1$ is nitro. In some embodiments, $R_1$ is optionally substituted $C_1$ to $C_6$ alkoxy. In some embodiments, $R_1$ is unsubstituted $C_1$ to $C_6$ alkoxy.

In some embodiments, $R_1$ is halogen. In some embodiments, $R_1$ is cyano. In some embodiments, $R_1$ is optionally substituted amido. In some embodiments, $R_1$ is optionally substituted ester. In some embodiments, $R_1$ is optionally substituted sulfonyl. In some embodiments, $R_1$ is optionally substituted S-sulfonamido. In some embodiments, $R_1$ is optionally substituted N-sulfonamido. In some embodiments, $R_1$ is optionally substituted sulfonate.

In some embodiments, $R_1$ is optionally substituted $C_1$ to $C_6$ alkyl. In some embodiments, $R_1$ is optionally substituted $C_2$ to $C_6$ alkenyl. In some embodiments, $R_1$ is optionally substituted $C_2$ to $C_6$ alkynyl. In some embodiments, $R_1$ is optionally substituted $C_3$ to $C_8$ carbocyclyl. In some embodiments, $R_1$ is optionally substituted $C_6$ to $C_{10}$ aryl. In some embodiments, $R_1$ is optionally substituted $C_3$ to $C_8$ heterocyclyl. In some embodiments, $R_1$ is optionally substituted $C_6$ to $C_{10}$ heteroaryl.

In some embodiments, $R_1$ is unsubstituted amido. In some embodiments, $R_1$ is unsubstituted ester. In some embodiments, $R_1$ is unsubstituted sulfonyl. In some embodiments, $R_1$ is unsubstituted S-sulfonamido. In some embodiments, $R_1$ is unsubstituted N-sulfonamido. In some embodiments, $R_1$ is unsubstituted sulfonate.

In some embodiments, $R_1$ is unsubstituted $C_1$ to $C_6$ alkoxy. In some embodiments, $R_1$ is unsubstituted $C_1$ to $C_6$ alkyl. In some embodiments, $R_1$ is unsubstituted $C_2$ to $C_6$ alkenyl.

In some embodiments, $R_1$ is unsubstituted $C_2$ to $C_6$ alkynyl. In some embodiments, $R_1$ is unsubstituted $C_3$ to $C_8$ carbocyclyl. In some embodiments, $R_1$ is unsubstituted $C_6$ to $C_{10}$ aryl. In some embodiments, $R_1$ is unsubstituted $C_3$ to $C_8$ heterocyclyl. In some embodiments, $R_1$ is unsubstituted $C_6$ to $C_{10}$ heteroaryl.

In some embodiments, $R_2$ is optionally substituted amino. In some embodiments, $R_2$ is unsubstituted amino. In some embodiments, $R_2$ is nitro. In some embodiments, $R_2$ is optionally substituted $C_1$ to $C_6$ alkoxy. In some embodiments, $R_2$ is unsubstituted $C_1$ to $C_6$ alkoxy.

In some embodiments, $R_2$ is halogen. In some embodiments, $R_2$ is cyano. In some embodiments, $R_2$ is optionally substituted amido. In some embodiments, $R_2$ is optionally substituted ester. In some embodiments, $R_2$ is optionally substituted sulfonyl. In some embodiments, $R_2$ is optionally substituted S-sulfonamido. In some embodiments, $R_2$ is optionally substituted N-sulfonamido. In some embodiments, $R_2$ is optionally substituted sulfonate.

In some embodiments, $R_2$ is optionally substituted $C_1$ to $C_6$ alkyl. In some embodiments, $R_2$ is optionally substituted $C_2$ to $C_6$ alkenyl. In some embodiments, $R_2$ is optionally substituted $C_2$ to $C_6$ alkynyl. In some embodiments, $R_2$ is optionally substituted $C_3$ to $C_8$ carbocyclyl. In some embodiments, $R_2$ is optionally substituted $C_6$ to $C_{10}$ aryl. In some embodiments, $R_2$ is optionally substituted $C_3$ to $C_8$ heterocyclyl. In some embodiments, $R_2$ is optionally substituted $C_6$ to $C_{10}$ heteroaryl.

In some embodiments, $R_2$ is unsubstituted amido. In some embodiments, $R_2$ is unsubstituted ester. In some embodiments, $R_2$ is unsubstituted sulfonyl. In some embodiments, $R_2$ is unsubstituted S-sulfonamido. In some embodiments, $R_2$ is unsubstituted N-sulfonamido. In some embodiments, $R_2$ is unsubstituted sulfonate. In some embodiments, $R_2$ is unsubstituted $C_1$ to $C_6$ alkoxy.

In some embodiments, $R_2$ is unsubstituted $C_1$ to $C_6$ alkyl. In some embodiments, $R_2$ is unsubstituted $C_2$ to $C_6$ alkenyl. In some embodiments, $R_2$ is unsubstituted $C_2$ to $C_6$ alkynyl. In some embodiments, $R_2$ is unsubstituted $C_3$ to $C_8$ carbocyclyl. In some embodiments, $R_2$ is unsubstituted $C_6$ to $C_{10}$ aryl. In some embodiments, $R_2$ is unsubstituted $C_3$ to $C_8$ heterocyclyl. In some embodiments, $R_2$ is unsubstituted $C_6$ to $C_{10}$ heteroaryl.

In some embodiments, $R_3$ is optionally substituted amino. In some embodiments, $R_3$ is unsubstituted amino. In some embodiments, $R_3$ is nitro. In some embodiments, $R_3$ is optionally substituted $C_1$ to $C_6$ alkoxy. In some embodiments, $R_3$ is unsubstituted $C_1$ to $C_6$ alkoxy. In some embodiments, $R_3$ is halogen. In some embodiments, $R_3$ is cyano.

In some embodiments, $R_3$ is optionally substituted amido. In some embodiments, $R_3$ is optionally substituted ester. In some embodiments, $R_3$ is optionally substituted sulfonyl. In some embodiments, $R_3$ is optionally substituted S-sulfonamido. In some embodiments, $R_3$ is optionally substituted N-sulfonamido. In some embodiments, $R_3$ is optionally substituted sulfonate.

In some embodiments, $R_3$ is optionally substituted $C_1$ to $C_6$ alkyl. In some embodiments, $R_3$ is optionally substituted $C_2$ to $C_6$ alkenyl. In some embodiments, $R_3$ is optionally substituted $C_2$ to $C_6$ alkynyl. In some embodiments, $R_3$ is optionally substituted $C_3$ to $C_8$ carbocyclyl. In some embodiments, $R_3$ is optionally substituted $C_6$ to $C_{10}$ aryl. In some embodiments, $R_3$ is optionally substituted $C_3$ to $C_8$ heterocyclyl. In some embodiments, $R_3$ is optionally substituted $C_6$ to $C_{10}$ heteroaryl.

In some embodiments, $R_3$ is unsubstituted amido. In some embodiments, $R_3$ is unsubstituted ester. In some embodiments, $R_3$ is unsubstituted sulfonyl. In some embodiments, $R_3$ is unsubstituted S-sulfonamido. In some embodiments, $R_3$ is unsubstituted N-sulfonamido. In some embodiments, $R_3$ is unsubstituted sulfonate.

In some embodiments, $R_3$ is unsubstituted $C_1$ to $C_6$ alkoxy. In some embodiments, $R_3$ is unsubstituted $C_1$ to $C_6$ alkyl. In some embodiments, $R_3$ is unsubstituted $C_2$ to $C_6$ alkenyl. In some embodiments, $R_3$ is unsubstituted $C_2$ to $C_6$ alkynyl. In some embodiments, $R_3$ is unsubstituted $C_3$ to $C_8$ carbocyclyl. In some embodiments, $R_3$ is unsubstituted $C_6$ to $C_{10}$ aryl. In some embodiments, $R_3$ is unsubstituted $C_3$ to $C_8$ heterocyclyl. In some embodiments, $R_3$ is unsubstituted $C_6$ to $C_{10}$ heteroaryl.

In some embodiments, $R_4$ is optionally substituted amino. In some embodiments, $R_4$ is unsubstituted amino. In some embodiments, $R_4$ is nitro. In some embodiments, $R_4$ is optionally substituted $C_1$ to $C_6$ alkoxy. In some embodiments, $R_4$ is unsubstituted $C_1$ to $C_6$ alkoxy. In some embodiments, $R_4$ is halogen. In some embodiments, $R_4$ is cyano.

In some embodiments, $R_4$ is optionally substituted amido. In some embodiments, $R_4$ is optionally substituted ester. In some embodiments, $R_4$ is optionally substituted sulfonyl. In some embodiments, $R_4$ is optionally substituted S-sulfonamido. In some embodiments, $R_4$ is optionally substituted N-sulfonamido. In some embodiments, $R_4$ is optionally substituted sulfonate.

In some embodiments, $R_4$ is optionally substituted $C_1$ to $C_6$ alkyl. In some embodiments, $R_4$ is optionally substituted $C_2$ to $C_6$ alkenyl. In some embodiments, $R_4$ is optionally substituted $C_2$ to $C_6$ alkynyl. In some embodiments, $R_4$ is optionally substituted $C_3$ to $C_8$ carbocyclyl. In some embodiments, $R_4$ is optionally substituted $C_6$ to $C_{10}$ aryl. In some embodiments, $R_4$ is optionally substituted $C_3$ to $C_8$ heterocyclyl. In some embodiments, $R_4$ is optionally substituted $C_6$ to $C_{10}$ heteroaryl. In some embodiments, $R_4$ is halogen.

In some embodiments, $R_4$ is unsubstituted amido. In some embodiments, $R_4$ is unsubstituted ester. In some embodiments, $R_4$ is unsubstituted sulfonyl. In some embodiments, $R_4$ is unsubstituted S-sulfonamido. In some embodiments, $R_4$ is unsubstituted N-sulfonamido. In some embodiments, $R_4$ is unsubstituted sulfonate.

In some embodiments, $R_4$ is unsubstituted $C_1$ to $C_6$ alkoxy. In some embodiments, $R_4$ is unsubstituted $C_1$ to $C_6$ alkyl. In some embodiments, $R_4$ is unsubstituted $C_2$ to $C_6$ alkenyl. In some embodiments, $R_4$ is unsubstituted $C_2$ to $C_6$ alkynyl. In some embodiments, $R_4$ is unsubstituted $C_3$ to $C_8$ carbocyclyl. In some embodiments, $R_4$ is unsubstituted $C_6$ to $C_{10}$ aryl. In some embodiments, $R_4$ is unsubstituted $C_3$ to $C_8$ heterocyclyl. In some embodiments, $R_4$ is unsubstituted $C_6$ to $C_{10}$ heteroaryl.

In some embodiments, $R_5$ is selected from H, deuterium, oxo, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments, $R_5$ is H. In some embodiments, $R_5$ is oxo. In some embodiments, $R_5$ is optionally substituted $C_1$ to $C_6$ alkyl. In some embodiments, $R_5$ is unsubstituted $C_1$ to $C_6$ alkyl. In some embodiments, $R_5$ is optionally substituted $C_2$ to $C_6$ alkenyl. In some embodiments, $R_5$ is unsubstituted $C_2$ to $C_6$ alkenyl. In some embodiments, $R_5$ is optionally substituted $C_2$ to $C_6$ alkynyl. In some embodiments, $R_5$ is unsubstituted $C_2$ to $C_6$ alkynyl. In some embodiments, $R_5$ is optionally substituted $C_3$ to $C_8$ carbocyclyl. In some embodiments, $R_5$ is unsubstituted $C_3$ to $C_8$ carbocyclyl. In some embodiments, $R_5$ is optionally substituted $C_6$ to $C_{10}$ aryl. In some embodiments, $R_5$ is unsubstituted $C_6$ to $C_{10}$ aryl. In some embodiments, $R_5$ is optionally substituted $C_3$ to $C_8$ heterocyclyl. In some embodiments, $R_5$ is unsubstituted $C_3$ to $C_8$ heterocyclyl. In some embodiments, $R_5$ is optionally substituted $C_6$ to $C_{10}$ heteroaryl. In some embodiments, $R_5$ is unsubstituted $C_6$ to $C_{10}$ heteroaryl.

In some embodiments, X is selected from $C(R_5)_2$, $CH(R_5)$, $CH_2$, C=O, and C=S. In some embodiments, X is $C(R_5)_2$. In some embodiments, X is $CH(R_5)$. In some embodiments, X is $CH_2$. In some embodiments, X is C=O. In some embodiments, X is C=S.

In some embodiments, Q is selected from $C(R_5)_2$, $CH(R_5)$, $CH_2$, C=O, C=S; S=O, and $SO_2$. In some embodiments, Q is selected from $CH_2$ and C=O. In some embodiments, Q is $C(R_5)_2$. In some embodiments, Q is $CH(R_5)$. In some embodiments, Q is $CH_2$. In some embodiments, Q is C=O. In some embodiments, Q is C=S. In some embodiments, Q is S=O. In some embodiments, Q is and $SO_2$.

In some embodiments, n is 1 or 2. In some embodiments, n is 1. In some embodiments, n is 2.

In some embodiments, the compound of Formula (I) is selected from:

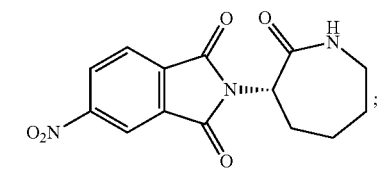

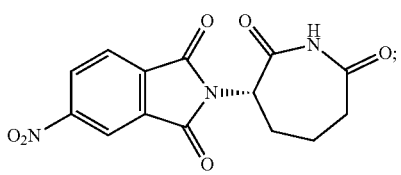

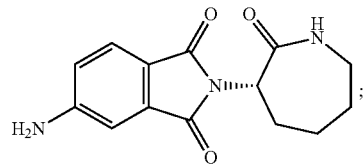

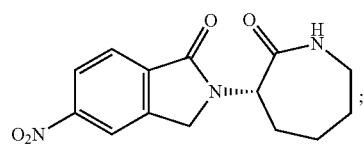

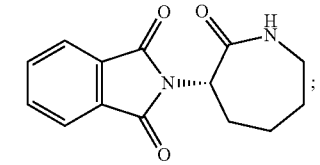

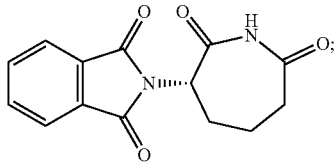

-continued

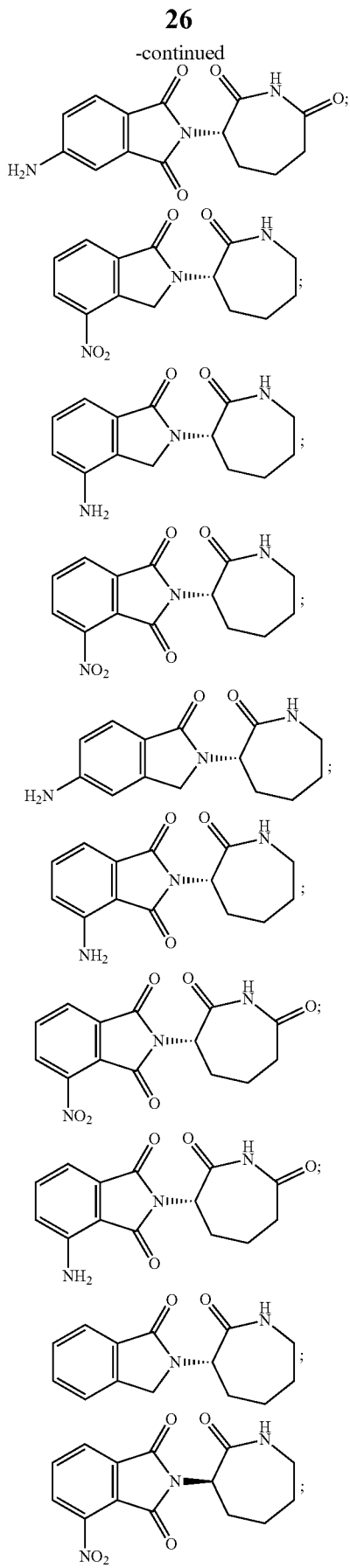

-continued

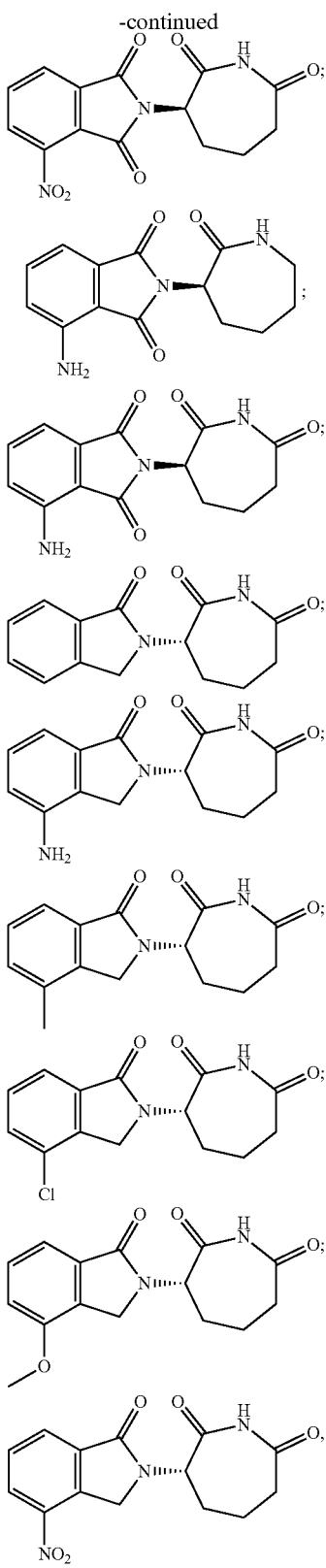

or pharmaceutically acceptable salts, solvates, and combinations of the foregoing.

Some embodiments provide a pharmaceutical composition comprising a compound of Formula (I) and at least one pharmaceutically acceptable carrier. Some embodiments provide a pharmaceutical composition comprising a pharmaceutically acceptable salt or a solvate of a compound of Formula (I) and at least one pharmaceutically acceptable carrier. The definitions for compounds of Formula (I) are the same as those set forth above.

Some embodiments provide methods of treating, ameliorating, or preventing a disease, disorder, or condition associated with protein function or imbalance, comprising administering a therapeutically effective amount of a compound of Formula (I). Some embodiments provide methods of treating, ameliorating, or preventing a disease, disorder, or condition associated with protein function or imbalance, comprising administering a pharmaceutically acceptable salt of solvate of a compound of Formula (I). The definitions for compounds of Formula (I) are the same as those set forth above.

In some embodiments, the disease, disorder, or condition selected from inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, and cancer. In some embodiments, the compound of Formula (I) is administered in combination with a second therapeutic agent.

Some embodiments provide methods of inhibiting protein activity, for example, cytokine activity, aiolos activity, and/or ikaros activity, comprising contacting a cell with a compound of Formula (I). Some embodiments provide methods of inhibiting cytokine activity, comprising contacting a cell with a pharmaceutically acceptable salt or a solvate of a compound of Formula (I). Some embodiments provide methods of inhibiting aiolos activity, comprising contacting a cell with a pharmaceutically acceptable salt or a solvate of a compound of Formula (I). Some embodiments provide methods of inhibiting ikaros activity, comprising contacting a cell with a pharmaceutically acceptable salt or a solvate of a compound of Formula (I). Some embodiments provide methods of inhibiting cell-cell adhesion, comprising contacting a cell with a pharmaceutically acceptable salt or a solvate of a compound of Formula (I). Some embodiments provide methods of modulating cell-cell adhesion, comprising contacting one or more cell(s) with a pharmaceutically acceptable salt or a solvate of a compound of Formula (I). The definitions for compounds of Formula (I) are the same as those set forth above. In some embodiments, the compound of Formula (I) is administered in combination with a second therapeutic agent.

Some embodiments provide methods of treating, ameliorating, or preventing a disease, disorder, or condition associated with protein malfunction, comprising administering a therapeutically effective amount of a compound of Formula (I):

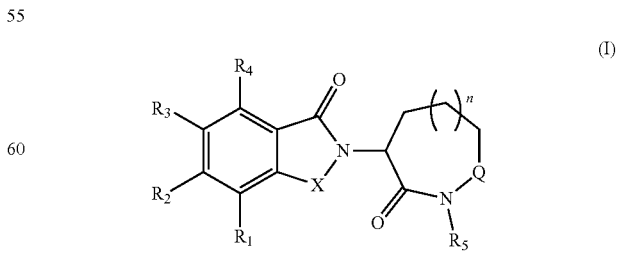

or a pharmaceutically acceptable salt or solvate thereof, to a subject in need thereof.

In some embodiments $R_1$, $R_2$, $R_3$, and $R_4$, are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments $R_5$ is selected from the group consisting of H, deuterium, oxo, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_6$ to $C_{10}$ heteroaryl.

In some embodiments X is selected from the group consisting of $C(R_5)_2$, $CH(R_5)$, $CH_2$, C=O, and C=S. In some embodiments Q is selected from the group consisting of $C(R_5)_2$, $CH(R_5)$, $CH_2$, C=O, C=S; S=O, and $SO_2$. In some embodiments n is 1 or 2.

In some embodiments, the disease, disorder, or condition is associated with casein kinase 1. In some embodiments, the disease, disorder, or condition is cancer. In some embodiments the cancer is selected from leukemia; lymphoma, bladder cancer, bone cancer, stomach cancer, colorectal cancer, brain cancer, breast cancer, cervical cancer, sarcoma, ocular cancer, oral cancer, renal cancer, liver cancer, lung cancer, non-small cell lung cancer, metastatic cancer, melanoma, mesothelioma, ovarian cancer, pancreatic cancer, prostate cancer, skin cancer, testicular cancer, throat cancer, thyroid cancer, uterine cancer.

In some embodiments the compound of Formula (I) is administered in combination with a second therapeutic agent. In some embodiments the second therapeutic agent is selected from the group consisting of anti-inflammatory agents, anti-cancer agents, immunostimulatory agents, and immunosuppressive agents. In some embodiments the second therapeutic agent is an anti-cancer agent.

In some embodiments Q is selected from the group consisting of $CH_2$ and C=O. In some embodiments Q is $CH_2$. In some embodiments Q is C=O. In some embodiments n is 1. In some embodiments n is 2. In some embodiments $R_5$ is H. In some embodiments $R_5$ is optionally substituted $C_1$ to $C_6$ alkyl. In some embodiments $R_5$ is optionally substituted $C_6$ to $C_{10}$ aryl. In some embodiments X is $CH_2$. In some embodiments X is C=O.

In some embodiments $R_1$ is $NH_2$. In some embodiments $R_1$ is $NO_2$. In some embodiments $R_1$ is $CH_3$. In some embodiments $R_1$ is chloro. In some embodiments $R_1$ is methoxy. In some embodiments $R_2$ is $NH_2$. In some embodiments $R_2$ is $NO_2$.

In some embodiments the compound of Formula (I) is in a form of a racemic mixture. In some embodiments the compound of Formula (I) has an S-configuration. In some embodiments the compound of Formula (I) has an R-configuration.

In some embodiments the compound of Formula (I) is selected from the group consisting of:

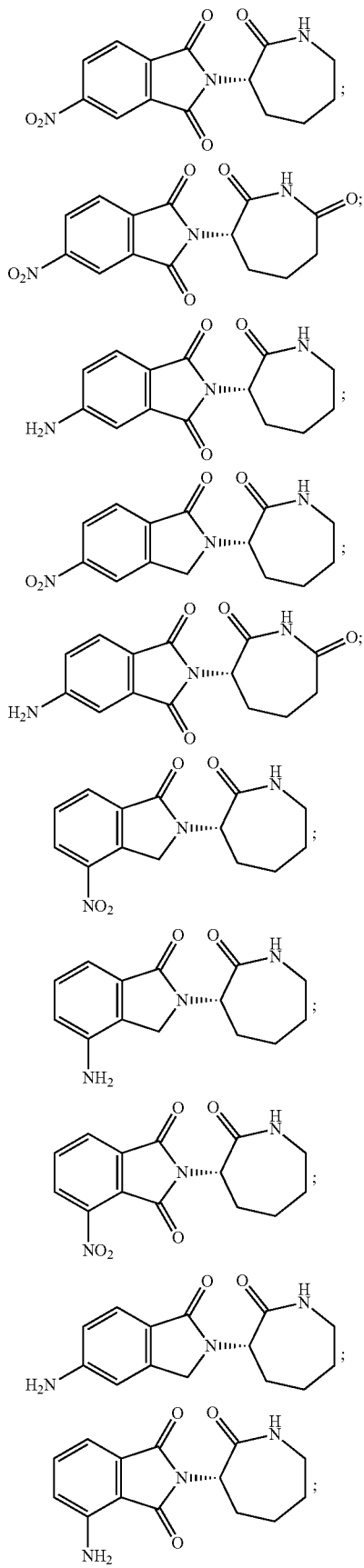

-continued

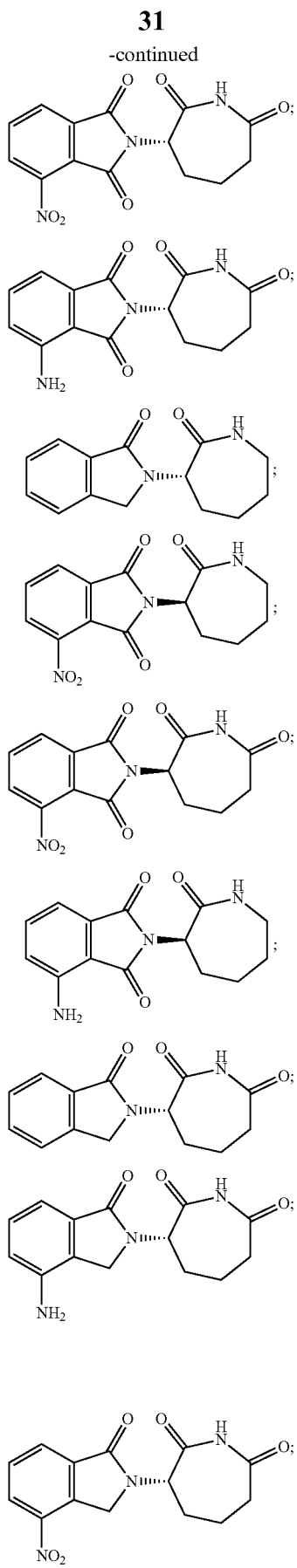

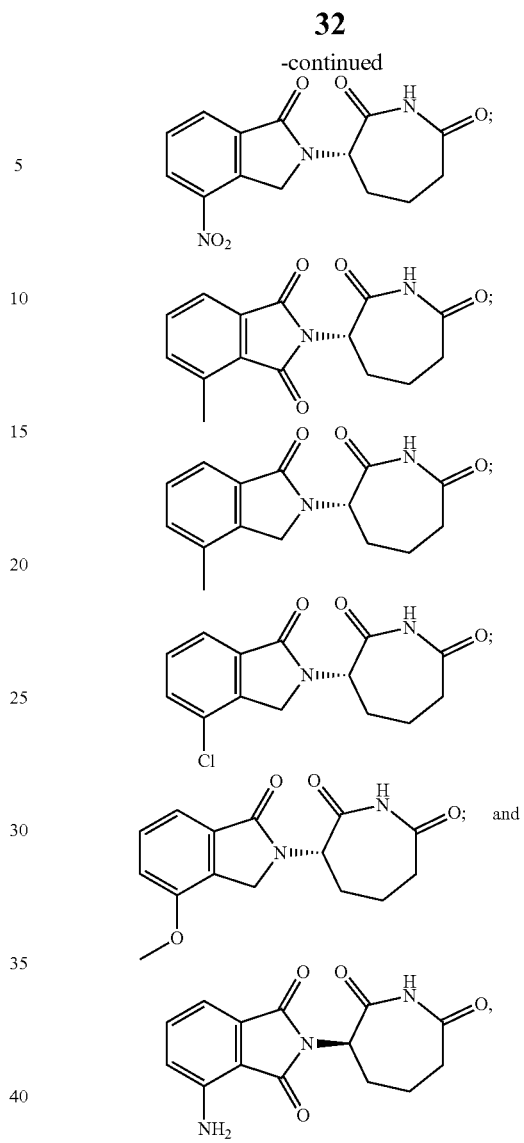

a pharmaceutically acceptable salts, solvates, and combinations of the foregoing.

In some embodiments the subject in need thereof is known to possess wild-type p53. In some embodiments the subject in need thereof is known to possess aberrant casein kinase 1.

One or more of the compounds of preferred embodiments can be provided in the form of pharmaceutically acceptable salts, solvates, active metabolites, tautomers, or prodrugs thereof. Some embodiments can be provided in pharmaceutical compositions comprising a therapeutically effective amount of the compound. In some embodiments, the pharmaceutical composition also contains at least one pharmaceutically acceptable inactive ingredient. The pharmaceutical composition can be formulated for intravenous injection, subcutaneous injection, oral administration, buccal administration, inhalation, nasal administration, topical administration, transdermal administration, ophthalmic administration, or otic administration. The pharmaceutical composition can be in the form of a tablet, a pill, a capsule, a liquid, an inhalant, a nasal spray solution, a suppository, a suspension, a gel, a colloid, a dispersion, a solution, an emulsion, an ointment, a lotion, an eye drop, or an ear drop.

The pharmaceutical compositions of preferred embodiments can further comprise one or more additional therapeutically active agents other than a compound of the preferred embodiments. Such agents can include, but are not limited to, anti-inflammatory agents, anti-cancer agents, immunostimulatory agents, and immunosuppressive agents.

Other objects, features, and advantages of the compounds, methods, and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, common organic abbreviations are defined as follows:
° C. Temperature in degrees Centigrade
DMSO Dimethylsulfoxide
g Gram(s)
h or hr Hour(s)
IL Interleukin
LPS Lipopolysaccharide
M-CSF Macrophage colony-stimulating factor
MS Mass spectrometry
mg Milligram(s)
mL Milliliter(s)
NaCl Sodium chloride
PBMC Peripheral blood mononuclear cell
PG Protecting group
ppt Precipitate
psi Pounds per square inch
RPMI Roswell Park Memorial Institute medium
rt Room temperature
TNF Tumor necrosis factor
μL Microliter(s)
wt. weight The term "protein malfunction," as used herein, refers to a protein or proteins not properly performing its intended biological function. For example, overexpression or underexpression and mutations in structure/function constitute a protein malfunction. Likewise, a protein or proteins that are expressed normally, and function normally, but are unable to perform their intended biological function (i.e., suppress tumor growth) are also malfunctioning proteins.

The term "protein homeostasis," as used herein, refers to the normal range of physiological levels of a protein or proteins.

The terms "co-administration" and similar terms as used herein are broad terms, and are to be given their ordinary and customary meaning to a person of ordinary skill in the art (and are not to be limited to a special or customized meaning), and refer without limitation to administration of the selected therapeutic agents to a single patient, and are intended to include treatment regimens in which the agents are administered by the same or different route of administration or at the same or different time.

The terms "effective amount" and "therapeutically effective amount" are broad terms, and are to be given their ordinary and customary meaning to a person of ordinary skill in the art (and are not to be limited to a special or customized meaning), and refer without limitation to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. Where a drug has been approved by the U.S. Food and Drug Administration (FDA) or a counterpart foreign medicines agency, a "therapeutically effective amount" optionally refers to the dosage approved by the FDA or its counterpart foreign agency for treatment of the identified disease or condition.

The term "pharmaceutical combination" as used herein is a broad term, and is to be given its ordinary and customary meaning to a person of ordinary skill in the art (and is not to be limited to a special or customized meaning), and refers without limitation to a product that results from the mixing or combining of more than one active ingredient and includes both fixed and non-fixed combinations of the active ingredients. The term "fixed combination" means that the active ingredients, e.g., a compound of a preferred embodiment and a co-agent, are both administered to a patient simultaneously in the form of a single entity or dosage. The term "non-fixed combination" means that the active ingredients, e.g., a compound of a preferred embodiment and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

As used herein, any "R" group(s) such as, without limitation, $R_2$, $R_3$, $R_4$, $R_5$, $R_6$, $R_9$, and $R_{10}$ represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^2$ and $R^3$, or $R^2$, $R^3$, or $R^4$, and the atom to which it is attached, are indicated to be "taken together" or "joined together" it means that they are covalently bonded to one another to form a ring:

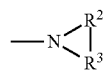

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents. If no substituents are indicated, it is meant that the indicated "optionally substituted" or "substituted" group may be individually and independently substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl; N-carbamyl, O-thiocarbamyl, N-thiocarbamyl, C-amido, N-amido, S-sulfonamido; N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, mono-substituted amino group and di-substituted amino group, and protected derivatives thereof.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, and hexyls. The alkyl group may be substituted or unsubstituted.

As used herein, "alkenyl" refers to an alkyl group, as defined herein, that contains in the straight or branched hydrocarbon chain one or more double bonds. An alkenyl group may be unsubstituted or substituted.

As used herein, "alkynyl" refers to an alkyl group as defined herein, that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl, and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than, one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "carbocyclyl" or "cyclic hydrocarbyl" refers to all carbon ring systems. Such systems can be unsaturated, can include some unsaturation, or can contain some aromatic portion, or be all aromatic. Carbocyclyl group can contain from 3 to 30 carbon atoms. A carbocyclyl group may be unsubstituted or substituted.

As used herein, "aryl" refers to a carbocyclic (all carbon) monocyclic or multicyclic aromatic ring system (including, e.g., fused; bridged; or spiro ring systems where two carbocyclic rings share a chemical bond, e.g., one or more aryl rings with one or more aryl or non-aryl rings) that has a fully delocalized pi-electron system throughout at least one of the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene, and azulene. An aryl group may be substituted or unsubstituted.

As used herein, "heterocyclyl" refers to mono- or polycyclic ring systems including at least one heteroatom (e.g., O, N, S). Such systems can be unsaturated, can include some unsaturation, or can contain some aromatic portion, or be all aromatic. A heterocyclyl group can contain from 3 to 30 atoms. A heterocyclyl group may be unsubstituted or substituted.

As used herein, "heteroaryl" refers to a monocyclic or multicyclic aromatic ring system (a ring system having a least one ring with a fully delocalized pi-electron system) that contain(s) one or more heteroatoms, that is, an element other than carbon, including but not limited to, nitrogen, oxygen, and sulfur, and at least one aromatic ring. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heteroalicyclic" or "heteroalicyclyl" refers to three-, four-, five-, six-, seven-, eight-, nine-, ten-, up to 18-membered monocycle, bicyclic, and tricycle ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatoms are independently selected from oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, and cyclic carbamates. When composed of two or more rings, the rings may be joined together in a fused fashion. Additionally, any nitrogens in a heteroalicyclic may be quaternized. Heteroalicyclyl or heteroalicyclic groups may be unsubstituted or substituted. Examples of such "heteroalicyclic" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

"Lower alkylene groups" are straight-chained —CH$_2$— tethering groups, forming bonds to connect molecular fragments via their terminal carbon atoms. Lower alkylene groups contain from 1 to 6 carbon atoms. Examples include but are not limited to methylene (—CH$_2$—), ethylene (—CH$_2$CH$_2$—), propylene (—CH$_2$CH$_2$CH$_2$—), and butylene (—CH$_2$CH$_2$CH$_2$CH$_2$—). A lower alkylene group can be substituted by replacing one or more hydrogen of the lower alkylene group with a substituent(s) listed under the definition of "substituted."

As used herein, "aralkyl" and "aryl(alkyl)" refer to an aryl group, as defined above, connected, as a substituent, via a lower alkylene group, as described above. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group, as defined above, connected, as a substituent, via a lower alkylene group, as defined above. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

A "(heteroalicyclyl)alkyl" is a heterocyclic or a heteroalicyclylic group, as defined above, connected, as a substituent, via a lower alkylene group, as defined above. The lower alkylene and heterocyclic or a heterocyclyl of a (heteroalicyclyl)alkyl may be substituted or unsubstituted: Examples include but are not limited to tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

As used herein, "alkoxy" refers to the formula —OR wherein R is an alkyl, an alkenyl, an alkynyl, a cycloalkyl, a cycloalkenyl or a cycloalkynyl, as defined above. A non-limiting list of alkoxys is methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, "acyl" refers to a hydrogen, alkyl, alkenyl, alkynyl, or aryl, as defined above, connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "aryloxy" and "arylthio" refers to RO— and RS—, in which R is an aryl, as defined above, such as but not limited to phenyl. Both an aryloxy and arylthio may be substituted or unsubstituted.

A "sulfenyl" group refers to an "—SR" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein X is a halogen.

A "trihalomethanesulfonamido" group refers to an "X$_3$CS(O)$_2$N(R$_A$)—" group wherein X is a halogen and R$_A$ hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl.

The term. "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanate" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An N-amido may be substituted or unsubstituted.

A "urea" group refers to a "—N(R$_A$R$_B$)—C(=O)—N(R$_A$R$_B$)—" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. A urea group may be substituted or unsubstituted.

A "thiourea" group refers to a "—N(R$_A$R$_B$)—C(=S)—N(R$_A$R$_B$)—" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. A thiourea group may be substituted or unsubstituted.

The term "halogen atom" or "halogen" as used herein, means any one of the radio-stable atoms of column 7 of the Periodic Table of the Elements, such as, fluorine, chlorine, bromine, and iodine.

In all of the definitions described herein, the terms used to define a new term are as previously defined herein.

Where the numbers of substituents is not specified (e.g., haloalkyl), there may be one or more substituents present. For example "haloalkyl" may include one or more of the same or different halogens. As another example, "C$_1$-C$_3$ alkoxyphenyl" may include one or more of the same or different alkoxy groups containing one, two, or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, *Biochem.* 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls (e.g., t-butoxycarbonyl (BOC), acetyl, or isobutyryl); arylalkylcarbonyls (e.g., benzyloxycarbonyl or benzoyl); substituted methyl ether (e.g., methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; Monomethoxytrityl (MNTr); 4,4'-dimethoxytrityl (DMTr); or 4,4',4''-trimethoxytrityl (TMTr)).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169471; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

The term "solvate" as used herein is a broad term, and is to be given its ordinary and customary meaning to a person of ordinary skill in the art (and is not to be limited to a special or customized meaning), and refers without limitation to mean that the solvent is complexed with a compound in a reproducible molar ratio, including, but not limited to, 0.5:1, 1:1, or 2:1. Thus, the term "pharmaceutically acceptable solvate," refers to a solvate wherein the solvent is one that does not cause significant irritation to an organism to which it is administered and does not abrogate the biological activity and properties of the compound.

The term "prodrug" as used herein is a broad term, and is to be given its ordinary and customary meaning to a person of ordinary skill in the art (and is not to be limited to a special or customized meaning), and refers without limitation to a compound or a pharmaceutical composition that can be administered to a patient in a less active or inactive form, which can then be metabolized in vivo into a more active metabolite. In certain embodiments, upon in vivo administration, a prodrug is chemically converted to the biologically, pharmaceutically, or therapeutically active form of the compound. In certain embodiments, a prodrug is enzymatically metabolized by one or more steps or processes to the biologically, pharmaceutically, or therapeutically active form of the compound.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns.

Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

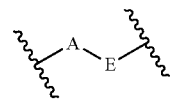

includes the substituent being oriented such that the A is attached at the leftmost attachment point of the molecule as well as the case in which A is attached at the rightmost attachment point of the molecule.

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of crystalline forms, amorphous phases, and/or pharmaceutically acceptable salts, solvates, hydrates, and conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. In specific embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Other forms in which the compounds of preferred embodiments can be provided include amorphous forms, milled forms and nano-particulate forms.

Likewise, it is understood that the compounds described herein, such as compounds of preferred embodiments, include the compound in any of the forms described herein (e.g., pharmaceutically acceptable salts, prodrugs, crystalline forms, amorphous form, solvated forms, enantiomeric forms, tautomeric forms, and the like).

Additional Therapeutic Agents

Some embodiments provide pharmaceutical compositions comprising a compound of Formula (I) and a pharmaceutically acceptable carrier. Some embodiments provide pharmaceutical compositions comprising a compound of Formula (I), a pharmaceutically acceptable carrier, and a second therapeutic agent. Some embodiments provide methods of inhibiting protein activity, including cytokine activity, aiolos activity, and/or ikaros activity, comprising contacting a cell with a compound of Formula (I). Some embodiments provide methods of inhibiting cytokine activity, comprising contacting a cell with a compound of Formula (I) in combination with a second therapeutic agent. Some embodiments-provide methods of inhibiting aiolos activity, comprising contacting a cell with a compound of Formula (I) in combination with a second therapeutic agent. Some embodiments provide methods of inhibiting ikaros activity, comprising contacting a cell with a compound of Formula (I) in combination with a second therapeutic agent. Some embodiments provide methods of modulating cell-cell adhesion, comprising contacting a cell with a compound of Formula (I) in combination with a second therapeutic agent.

Some embodiments provide methods of treating, ameliorating, or preventing a disease, disorder, or condition associated with protein function or imbalance, comprising administering a therapeutically effective amount of a compound of Formula (I). Some embodiments provide methods of treating, ameliorating, or preventing a disease, disorder, or condition associated with protein function or imbalance, comprising administering a therapeutically effective amount of a compound of Formula (I) in combination with a second therapeutic agent. Some embodiments provide methods of treating ameliorating, or preventing a disease, disorder, or condition associated with cytokines, comprising administering a therapeutically effective amount of a compound of Formula (I) in combination with a second therapeutic agent. Some embodiments provide methods of treating, ameliorating, or preventing a disease, disorder, or condition associated with ikaros, comprising administering a therapeutically effective amount of a compound of Formula (I) in combination with a second therapeutic agent. Some embodiments provide methods of treating, ameliorating, or preventing a disease, disorder, or condition associated with aiolos, comprising administering a therapeutically effective amount of a compound of Formula (I) in combination with a second therapeutic agent. Some embodiments provide methods of treating, ameliorating, or preventing a disease, disorder, or condition associated with cell-cell adhesion, comprising administering a therapeutically effective amount of a compound of Formula (I) in combination with a second therapeutic agent.

In some embodiments, the second therapeutic agent is an anti-inflammatory agent. In some embodiments, the second therapeutic agent is a non-steroidal anti-inflammatory agent. In some embodiments, the second therapeutic agent is an anti-cancer agent. In some embodiments, the second therapeutic agent is an immunostimulatory agent. In some embodiments, the second therapeutic agent is an immunosuppressive agent. In some embodiments, the second therapeutic agent is an antibody.

In some embodiments, the second therapeutic agent is selected from aspirin; diflunisal; salsalate; acetaminophen; ibuprofen; dexibuprofen; naproxen; fenoprofen; ketoprofen; dexketoprofen; flurbiprofen; oxaprozin; loxoprofen; indomethacin; tolmetin; sulindac; etodolac; ketorolac; diclofenac; aceclofenac; nabumetone; enolic acid; piroxicam; meloxicam; tenoxicam; droxicam; lornoxicam; isoxicam; mefenamic acid; meclofenamic acid; flufenamic acid; tolfenamic acid; sulfonanilides; clonixin; licofelone; dexamethasone; and prednisone.

In some embodiments, the second therapeutic agent is selected from mechlorethamine; cyclophosphamide; melphalan; chlorambucil; ifosfamide; busulfan; N-nitroso-N-methylurea (MNU); carmustine (BCNU); lomustine (CCNU); semustine (MeCCNU); fotemustine; streptozotocin; dacarbazine; mitozolomide; temozolomide thiotepa; mytomycin; diaziquone (AZQ); cisplatin; carboplatin; and oxaliplatin.

In some embodiments, the second therapeutic agent is selected from vincristine; vinblastine; vinorelbine; vindesine; vinflunine; paclitaxel; docetaxel; etoposide; teniposide; tofacitinib; ixabepilone; irinotecan; topotecan; camptothecin; doxorubicin; mitoxantrone; and teniposide.

In some embodiments, the second therapeutic agent is selected from actinomycin; bleomycin; plicamycin; mitomycin; daunorubicin; epirubicin; idarubicin; pirarubicin; aclarubicin; mitoxantrone; cyclophosphamide; methotrexate; 5-fluorouracil; prednisolone; folinic acid; methotrexate; melphalan; capecitabine; mechlorethamine; uramustine;

melphalan; chlorambucil; ifosfamide; bendamustine; 6-mercaptopurine; and procarbazine.

In some embodiments, the second therapeutic agent is selected from cladribine; pemetrexed; fludarabine; gemcitabine; hydroxyurea; nelarabine; cladribine; clofarabine; ytarabine; decitabine; cytarabine; cytarabine liposomal; pralatrexate; floxuridine; fludarabine; colchicine; thioguanine; cabazitaxel; larotaxel; ortataxel; tesetaxel; aminopterin; pemetrexed; pralatrexate; raltitrexed; pemetrexed; carmofur; and floxuridine.

In some embodiments, the second therapeutic agent is selected from azacitidine; decitabine; hydroxycarbamide; topotecan; irinotecan; belotecan; teniposide; aclarubicin; epirubicin; idarubicin; amrubicin; pirarubicin; valrubicin; zorubicin; mitoxantrone; pixantrone; mechlorethamine; chlorambucil; prednimustine; uramustine; estramustine; carmustine; lomustine; fotemustine; nimustine; ranimustine; carboquone; thioTEPA; triaziquone; and triethylenemelamine.

In some embodiments, the second therapeutic agent is selected from nedaplatin; satraplatin; procarbazine; dacarbazine; temozolomide; altretamine; mitobronitol; pipobroman; actinomycin; bleomycin; plicamycin; aminolevulinic acid; methyl aminolevulinate; efaproxiral; talaporfin; temoporfin; verteporfin; alvocidib; seliciclib; palbociclib; bortezomib; carfilzomib; anagrelide; masoprocol; olaparib; belinostat; panobinostat; romidepsin; vorinosta; idelalisib; atrasentan; bexarotene; testolactone; amsacrine; trabectedin; alitretinoin; tretinoin; demecolcine; elsamitrucin; etoglucid; lonidamine; lucanthone; mitoguazone; mitotane; oblimersen; omacetaxine mepesuccinate; and eribulin.

In some embodiments, the second therapeutic agent is selected from azathioprine; Mycophenolic acid; leflunomide; teriflunomide; tacrolimus; cyclosporin; pimecrolimus; abetimus; gusperimus; lenalidomide; pomalidomide; thalidomide; anakinra; sirolimus; everolimus; ridaforolimus; temsirolimus; umirolimus; zotarolimus; eculizumab; adalimumab; afelimomab; certolizumab pegol; golimumab; infliximab; nerelimomab; mepolizumab; omalizumab; faralimomab; elsilimomab; lebrikizumab; ustekinumab; etanercept; otelixizumab; teplizumab; visilizumab; clenoliximab; keliximab; zanolimumab; efalizumab; erlizumab; obinutuzumab; rituximab; and ocrelizumab.

In some embodiments, the second therapeutic agent is selected from pascolizumab; gomiliximab; lumiliximab; teneliximab; toralizumab; aselizumab; galiximab; gavilimomab; ruplizumab; belimumab; blisibimod; ipilimumab; tremelimumab; bertilimumab; lerdelimumab; metelimumab; natalizumab; tocilizumab; odulimomab; basiliximab; daclizumab; inolimomab; zolimoma; atorolimumab; cedelizumab; fontolizumab; maslimomab; morolimumab; pexelizumab; reslizumab; rovelizumab; siplizumab; talizumab; telimomab; vapaliximab; vepalimomab; abatacept; belatacept; pegsunercept; aflibercept; alefacept; and rilonacept.

Dosing Regimes

In some embodiments, about 1 mg to about 5 grams of a compound of Formula (I) is administered each day. In some embodiments, about 2 mg to about 2 grams of a compound of Formula (I) is administered each day. In some embodiments, about 5 mg to about 1 gram of a compound of Formula (I) is administered each day. In some embodiments, about 10 mg to about 800 milligrams of a compound of Formula (I) is administered each day. In some embodiments, about 20 mg to about 600 milligrams of a compound of Formula (I) is administered each day. In some embodiments, about 30 mg to about 400 milligrams of a compound of Formula (I) is administered each day. In some embodiments, about 40 mg to about 200 milligrams of a compound of Formula (I) is administered each day. In some embodiments, about 50 mg to about 100 milligrams of a compound of Formula (I) is administered each day.

In some embodiments, about 1 mg to about 5 grams of a compound of Formula (I) is administered each week. In some embodiments, about 2-mg to about 2 grams of a compound of Formula (I) is administered each week. In some embodiments, about 5 mg to about 1 gram of a compound of Formula (I) is administered each week. In some embodiments, about 10 mg to about 800 milligrams of a compound of Formula (I) is administered each week. In some embodiments, about 20 mg to about 600 milligrams of a compound of Formula (I) is administered each week. In some embodiments, about 30 mg to about 400 milligrams of a compound of Formula (I) is administered each week. In some embodiments, about 40 mg to about 200 milligrams of a compound of Formula (I) is administered each week. In some embodiments, about 50 mg to about 100 milligrams of a compound of Formula (I) is administered each week.

In some embodiments, about 1 mg to about 5 grams of a compound of Formula (I) is administered each cycle of treatment. In some embodiments, about 2 mg to about 2 grams of a compound of Formula (I) is administered each cycle of treatment. In some embodiments, about 5 mg to about 1 gram of a compound of Formula (I) is administered each cycle of treatment. In some embodiments, about 10 mg to about 800 milligrams of a compound of Formula (I) is administered each cycle of treatment. In some embodiments, about 20 mg to about 600 milligrams of a compound of Formula (I) is administered each cycle of treatment. In some embodiments, about 30 mg to about 400 milligrams of a compound of Formula (I) is administered each cycle of treatment. In some embodiments, about 40 mg to about 200 milligrams of a compound of Formula (I) is administered each cycle of treatment. In some embodiments, about 50 mg to about 100 milligrams of a compound of Formula (I) is administered each cycle of treatment.

In some embodiments, a compound of Formula (I) is administered at least once per day. In some embodiments, a compound of Formula (I) is administered at least twice per day. In some embodiments, a compound of Formula (I) is administered at least three times per day. In some embodiments, a compound of Formula (I) is administered at least four times per day.

In some embodiments, a compound of Formula (I) is administered at least once per week. In some embodiments, a compound of Formula (I) is administered at least twice per week. In some embodiments, a compound of Formula (I) is administered at least three times per week. In some embodiments, a compound of Formula (I) is administered at least four times per week.

In some embodiments, each cycle of treatment lasts 1 day.
In some embodiments, each cycle of treatment lasts 2 days.
In some embodiments, each cycle of treatment lasts 3 days.
In some embodiments, each cycle of treatment lasts 4 days.
In some embodiments, each cycle of treatment lasts 5 days.
In some embodiments, each cycle of treatment lasts 6 days.
In some embodiments, each cycle of treatment lasts 7 days.
In some embodiments, each cycle of treatment lasts 8 days.
In some embodiments, each cycle of treatment lasts 9 days.
In some embodiments, each cycle of treatment lasts 10 days.
In some embodiments, each cycle of treatment lasts 11 days.
In some embodiments, each cycle of treatment lasts 12 days.
In some embodiments, each cycle of treatment lasts 13 days.
In some embodiments, each cycle of treatment lasts 14 days.

In some embodiments, each cycle of treatment has at least one day between administrations of a compound of Formula (I). In some embodiments, each cycle of treatment has at least two days between administrations of a compound of Formula (I). In some embodiments, each cycle of treatment has at least three days between administrations of a compound of Formula (I). In some embodiments, each cycle of treatment has at least four days between administrations of a compound of Formula (I). In some embodiments, each cycle of treatment has at least five days between administrations of a compound of Formula (I). In some embodiments, each cycle of treatment has at least six days between administrations of a compound of Formula (I). In some embodiments, each cycle of treatment has at least seven days between administrations of a compound of Formula (I).

In some embodiments, a compound of Formula (I) is provided intravenously over about 10 minutes. In some embodiments; a compound of Formula (I) is provided intravenously over about 20 minutes. In some embodiments, a compound of Formula (I) is provided intravenously over about 30 minutes. In some embodiments, a compound, of Formula (I) is provided intravenously over about 1 hour. In some embodiments, a compound of Formula (I) is provided intravenously over about 1.5 hours. In some embodiments, a compound of Formula (I) is provided intravenously over about 2 hours. In some embodiments, a compound of Formula (I) is provided intravenously over about 2.5 hours. In some embodiments, a compound of Formula (I) is provided intravenously over about 3 hours. In some embodiments, a compound of Formula (I) is provided intravenously over about 3.5 hours. In some embodiments, a compound of Formula (I) is provided intravenously over about 4 hours.

EXAMPLES

Additional embodiments are disclosed in further detail in the following examples, which are not in any way intended to limit the scope of the claims.

Characterization of the compounds disclosed herein was performed with Bruker AV-500 and Bruker DRX-500 NMR spectrometers and a Perkin Elmer PE-SCIEX API-150 mass spectrometer.

Synthesis

5-Nitro-2-[(3S)-2-oxoazepan-3-yl]isoindoline-1,3-dione (Compound 12)

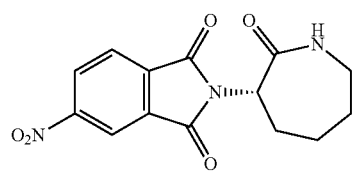 [SMILES: O=C1NCCCC[C@@H]1N1C(=O)c2ccc([N+](=O)[O-])cc2C1=O]

(S)-3-Aminoazepan-2-one (0.398 g, 3.11 mmol) was added to a mixture of 5-nitroisobenzofuran-1,3-dione (0.600 g, 3.11 mmol) and acetic acid (2 mL) in acetonitrile (20 mL). The reaction mixture was stirred at 70° C. overnight. Sodium acetate (0.382 g, 4.66 mmol) and additional acetic acid (4 mL) was then added to the reaction mixture. After continued heating for 1 day at 70° C., the solution was cooled to room temperature and evaporated under vacuum. The residue was dissolved in ethyl acetate (150 mL) and washed with saturated sodium bicarbonate (2×100 mL). The solution was dried over magnesium sulfate, filtered, and concentrated under vacuum to afford the title compound as an off-white solid (0.466 g, 49% yield). MS (M+1) 304. $^1$H NMR (DMSO-d$_6$) δ 8.65 (d, 1H, J=0.017), 8.51 (s, 1H), 8.15 (d, 1H, J=0.017), 4.90 (dd, 1H, J=0.021), 3.24 (m, 1H), 3.14 (m, 1H), 2.37 (m, 1H), 2.04 (m, 2H), 1.81 (m, 1H), 1.69 (m, 1H), 1.32 (m, 1H).

2-[(3S)-2,7-Dioxoazepan-3-yl]-5-nitro-isoindoline-1,3-dione (Compound 13)

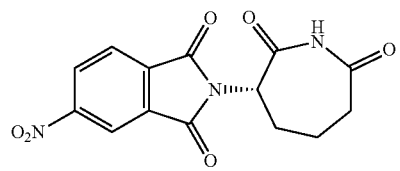 [SMILES: O=C1CCC[C@H](N2C(=O)c3ccc([N+](=O)[O-])cc3C2=O)C(=O)N1]

Potassium permanganate (0.261 g, 1.65 mmol) was added to a mixture of 5-nitro-2-(2-oxoazepan-3-yl)isoindoline-1,3-dione (0.100 g, 0.330 mmol) in sulfuric acid (0.5 mL), water (1 mL), and acetic acid (1 mL). The resulting mixture was stirred for 1 day at ambient temperature. Ethyl acetate (100 mL) was added, and the organic layer was washed with water (3×50 mL) then saturated sodium bicarbonate (2×50 mL). The solution was dried over magnesium sulfate, filtered, and concentrated under vacuum to afford the title compound as a white solid (0.049 g, 47% yield). MS (M+1) 318. $^1$H NMR (DMSO-d6) δ 10.87 (s, 1H), 8.67 (d, J=0.17), 8.56 (s, 1H), 8.19 (d, 1H, J=0.16), 5.30 (dd, 1H, J=0.24), 3.15 (m, 1H), 2.67 (m, 1H), 2.51 (m, 1H), 2.17 (m, 1H), 1.97 (m, 1H), 1.89 (m, 1H).

5-Amino-2-[(3S)-2-oxoazepan-3-yl]isoindoline-1,3-dione (Compound 14)

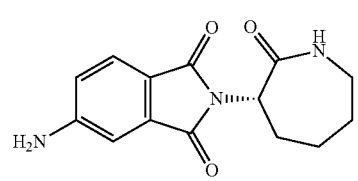 [SMILES: Nc1ccc2c(c1)C(=O)N([C@H]1CCCCNC1=O)C2=O]

5-Nitro-2-(2-oxoazepan-3-yl)isoindoline-1,3-dione (0.030 g, 0.106 mmol) was dissolved in ethanol (6 mL) then hydrogen gas was bubbled through the solution for 10 seconds. To the solution was added 10 wt. % palladium on carbon (0.020 g) and the mixture was hydrogenated under 20-40 psi of hydrogen for 3 hours. The mixture was filtered through celite, and the filtrate was concentrated under vacuum to afford the title compound as a light yellow solid (0.024 g, 89% yield). MS (M+1) 274.

5-Nitro-2-[(3S)-2-oxoazepan-3-yl]isoindolin-1-one (Compound 6)

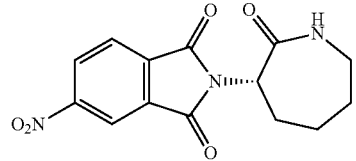 [SMILES: O=C1NCCCC[C@@H]1N1C(=O)c2ccc([N+](=O)[O-])cc2C1=O]

A solution of methyl 2-(bromomethyl)-4-nitro-benzoate (1.00 g, 3.65 mmol), (S)-3-aminoazepan-2-one (0.468 g, 3.65 mmol) and triethyl amine (1 mL, 7 mmol) in dimethyl formamide (10 mL) was stirred for 1 day at 50° C. The solution was then cooled to room temperature, water (50 mL) was added, and the mixture cooled in an ice water bath for 10 minutes. The resulting precipitate was filtered and dried to afford the title compound as an off-white solid (0.864 g, 82% yield). MS (M+Na) 312. $^1$H NMR (DMSO-d6) δ 8.52 (s, 1H), 8.34 (d, 1H, J=0.016), 7.93 (d, 1H, J=0.016), 7.86 (bs, 1H), 4.94 (d, 1H, J=0.022), 4.82 (d, 1H, J=0.036), 4.61 (d, 1H, J=0.036), 3.26 (m, 2H), 3.12 (m, 1H), 2.02 (m, 2H), 1.82 (m, 1H), 1.71 (m, 1H), 1.30 (m, 1H).

2-[(3S)-2-Oxoazepan-3-yl]isoindoline-1,3-dione (Compound 15)

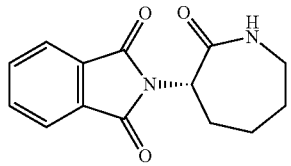 [SMILES: O=C1NCCCC[C@@H]1N1C(=O)c2ccccc2C1=O]

The title compound was afforded as a white solid (0.219 g, 63% yield) using the methods described above. MS (M+1) 259. $^1$H NMR (DMSO-d6) δ 7.85 (dd, 2H, J=0.011), 7.70 (dd, 2H, J=0.011), 5.97 (bs, 1H), 4.94 (dd, 1H, J=0.024). 3.31 (m, 1H), 3.28 (m, 1H), 2.71 (m, 1H), 2.17 (m, 1H), 2.04 (m, 1H), 1.91 (m, 1H), 1.71 (m, 1H), 1.69 (m, 1H).

2-[(3S)-2,7-Dioxoazepan-3-yl]isoindoline-1,3-dione (Compound 1)

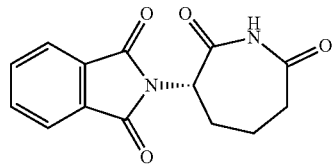 [SMILES: O=C1CCC[C@H](N2C(=O)c3ccccc3C2=O)C(=O)N1]

The title compound was afforded using the methods described above. The crude product was purified by silica gel column chromatography (hexanes/ethyl acetate, 4:1) to afford the title compound as a white solid (0.068 g, 65% yield). MS (M+1) 273. $_1$H NMR (DMSO-d6) δ 10.82 (s, 1H), 7.93 (m, 2H), 7.90 (m, 2H), 5.23 (dd, 1H), 3.12 (m, 1H), 2.67 (m, 1H), 2.53 (m, 1H), 2.12 (m, 1H), 1.98 (m, 1H), 1.95 (m, 1H).

5-Amino-2-[(3S)-2,7-dioxoazepan-3-yl]isoindoline-1,3-dione (Compound 2)

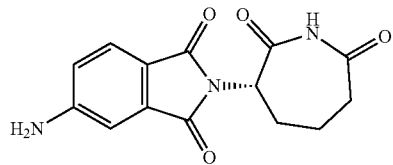 [SMILES: Nc1ccc2c(c1)C(=O)N([C@H]1CCCC(=O)NC1=O)C2=O]

The title compound was afforded as a yellow solid (0.009 g, 33% yield) using the methods described above. MS (M+1) 288.

4-Nitro-2-[(3S)-2-oxoazepan-3-yl]isoindolin-1-one (Compound 3)

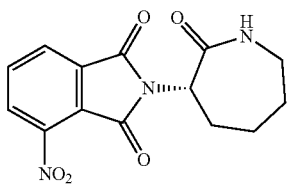

The title compound was afforded as an off-white solid (326 g, 56% yield) using the methods described above. MS (M+Na) 312. $^1$H NMR (DMSO-d6) δ 8.45 (d, 1H, J=0.016), 8.15 (d, 1H, J=0.015), 7.88 (bs, 1H), 7.82 (dd, 1H, J=0.016), 5.12 (d, 1H, J=0.038), 4.96 (d, 1H, J=0.023), 4.92 (d, 1H, J=0.038), 3.26 (m, 2H), 3.12 (m, 1H), 2.02 (m, 2H), 1.92 (m, 1H), 1.84 (m, 1H), 1.73 (m, 1H), 1.31 (m, 1H).

4-Amino-2-[(3S)-2-oxoazepan-3-yl]isoindolin-1-one (Compound 4)

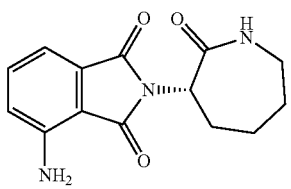 [SMILES: Nc1cccc2c1C(=O)N([C@H]1CCCCNC1=O)C2=O]

The title compound was afforded as a pale yellow solid (0.013 g, 73% yield) using the methods described above. MS (M+1) 260. $^1$H NMR (DMSO-d6) δ 7.78 (bs, 1H), 7.14 (dd, 1H, J=0.016), 6.86 (d, 1H, J=0.015), 6.75 (d, 1H, J=0.015), 5.39 (bs, 2H), 4.88 (d, 1H, J=0.021), 4.50 (d, 1H, J=0.034), 4.20 (d, 1H, J=0.034), 3.23 (m, 1H), 3.12 (m, 1H), 1.99 (m, 2H), 1.83 (m, 1H), 1.77 (m, 1H), 1.31 (m, 1H).

4-Nitro-2-[(3S)-2-oxoazepan-3-yl]isoindoline-1,3-dione (Compound 5)

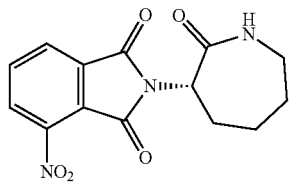

The title compound was afforded as a pale yellow solid (0.460 g, 49% yield) using the methods described above. MS (M+Na) 326. $^1$H NMR (DMSO-d6) δ 8.32 (d, 1H, J=0.16), 8.31 (d, 1H, J=0.016), 8.19 (dd, 1H, J=0.015), 7.95 (bs, 1H), 4.86 (dd, 1H, J=0.023), 123 (m, 1H), 3.12 (m, 1H), 2.36 (m, 1H), 2.03 (m, 1H), 1.81 (m, 1H), 1.66 (m, 1H), 1.34 (m, 1H).

5-Amino-2-[(3S)-2-oxoazepan-3-yl]isoindolin-1-one (Compound 7)

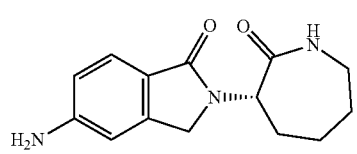 [SMILES: Nc1ccc2c(c1)CN([C@H]1CCCCNC1=O)C2=O]

The title compound was afforded as a light beige solid (0.065 g, 87% yield) using the methods described above. MS (M+1) 260.

4-Amino-2-[(3S)-2-oxoazepan-3-yl]isoindoline-1,3-dione (Compound 8)

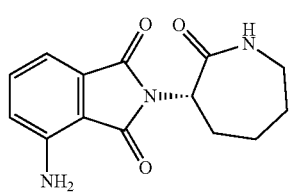 [SMILES: Nc1cccc2c1C(=O)N([C@H]1CCCCNC1=O)C2=O]

The title compound was afforded as a yellow solid (0.037 g, 61% yield) using the methods described above. MS (M+Na) 296.

2-[(3S)-2,7-Dioxoazepan-3-yl]-4-nitro-isoindoline-1,3-dione (Compound 9)

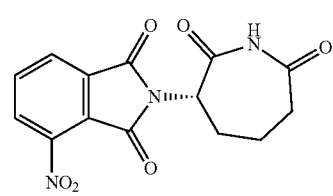 [SMILES: O=C1CCC[C@H](N2C(=O)c3cccc([N+](=O)[O-])c3C2=O)C(=O)N1]

The title compound was afforded using the methods described above. The crude product was obtained, then purified by silica gel column chromatography (DCM/MeOH, 10:1) to afford the title compound as a white solid (0.025 g, 28% yield). MS (M+Na) 341.

4-Amino-2-[(3S)-2,7-dioxoazepan-3-yl]isoindoline-1,3-dione (Compound 10)

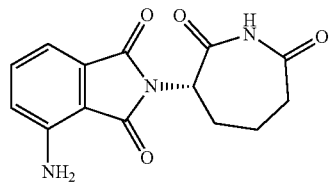

The title compound was afforded as a light yellow solid (0.018 g, 94% yield) using the methods described above. MS (M+Na) 310.

2-(2-Oxoazepan-3-yl)isoindolin-1-one (Compound 11)

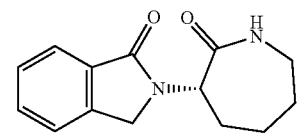 [SMILES: O=C1NCCCC[C@@H]1N1Cc2ccccc2C1=O]

The title compound was afforded as a white solid (0.143 g, 25% yield) using the methods described above. MS (M+Na) 245. $^1$H NMR (DMSO-d6) δ 7.80 (bs, 1H), 7.69 (d, 1H, J=0.15), 7.60 (d, 2H, J=0.008), 7.49 (dd, 1H, J=0.015, 0.008).

4-Nitro-2-[(3R)-2-oxoazepan-3-yl]isoindoline-1,3-dione (Compound 17)

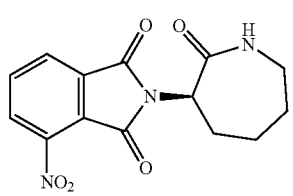 [SMILES: O=C1NCCCC[C@H]1N1C(=O)c2cccc([N+](=O)[O-])c2C1=O]

The title compound was afforded as an off-white solid (0.286 g, 54% yield) using the methods described herein. MS (M+Na) 326.

2-[(3R)-2,7-Dioxoazepan-3-yl]-4-nitro-isoindoline-1,3-dione (Compound 18)

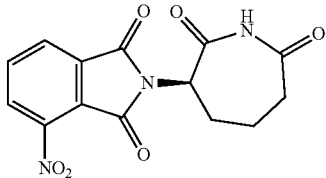

The title compound was afforded as an off-white solid (0.025 g, 24% yield) using the methods described above. MS (M+Na) 342.

4-Amino-2-[(3R)-2-oxoazepan-3-yl]isoindoline-1,3-dione (Compound 19)

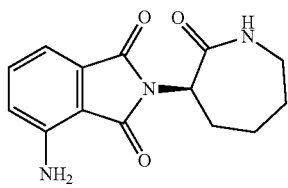 [SMILES: Nc1cccc2c1C(=O)N([C@@H]1CCCCNC1=O)C2=O]

The title compound was afforded as a yellow solid (0.022 g, 96% yield) using the methods described above. MS (M+1) 274.

4-Amino-2-[(3R)-2,7-dioxoazepan-3-yl]isoindoline-1,3-dione (Compound 20)

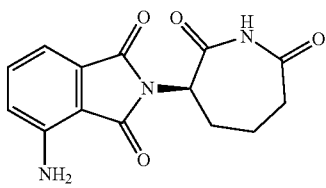 [SMILES: Nc1cccc2c1C(=O)N([C@@H]1CCCC(=O)NC1=O)C2=O]

The title compound was afforded as a yellow solid (0.019 g, 91% yield) using the methods described above. MS (M+Na) 310. $^1$H NMR (DMSO-d6) δ 10.76 (bs, 1H), 7.57 (dd, 1H, J=0.014), 7.01 (d, H, J=0.014), 6.99 (d, H, J=0.014), 6.48 (bs, 2H), 5.12 (dd, 1H, J=0.024), 3.10 (m, 1H), 2.68 (m, 1H), 2.53 (m, 1H), 2.07 (m, 1H), 2.05 (m, 1H), 1.98 (m, 1H).

(2S)-2-[(3S)-2,7-Dioxo-3-azepinyl]-2,4-diaza-2H-indene-1,3-dione (Compound 16)

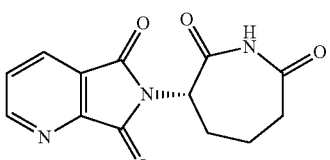

The title compound was afforded as a white solid (0.229 g, 9% yield) using the methods described above. MS (M+Na) 282.

(2S)-2-[(3S)-2-Oxo-3-azepinyl]-4-methyl-2H-isoindole-1,3-dione (Compound 21)

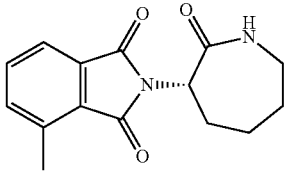 [SMILES: Cc1cccc2c1C(=O)N([C@H]1CCCCNC1=O)C2=O]

The title compound was afforded as an off white solid (0.527 g, 78% yield) using the methods described above. MS (M+1) 273.

(3S)-3-[(2S)-4-Methyl-3-oxo-2H-isoindol-2-oyl]-2,7-azepinedione (Compound 23)

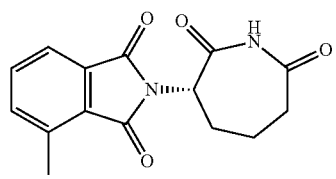 [SMILES: Cc1cccc2c1C(=O)N([C@H]1CCCC(=O)NC1=O)C2=O]

The title compound was afforded as a white solid (0.062 g, 17% yield) using the methods described above. MS (M+Na) 309. $^1$H NMR (DMSO-d6) δ 10.82 (s, 1H), 7.73 (m, 2H), 7.66 (d, 1H), 5.20 (dd, 1H), 3.32 (s, 3H), 3.14 (m, 1H), 2.63 (m, 2H), 2.12 (m, 1H), 1.98 (m, 1H), 1.89 (m, 1H).

(3S)-3-[(2S)-4-Nitro-2-isoindolinoyl]-2,7-azepinedione (Compound 29)

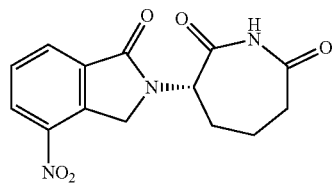 [SMILES: O=C1CCC[C@H](N2Cc3c(cccc3[N+](=O)[O-])C2=O)C(=O)N1]

(3S)-3-[(2S)-4-Nitro-2-isoindolinoyl]-2-azepinone (1.81 g, 6.26 mmol) was slurried in fluorobenzene (60 mL) with 200 drops of wet dimethyl sulfoxide (prepared by adding 2 drops water to 10 ml dimethyl sulfoxide). Dess-martin periodinane (4.00 g, 9.39 mmol) was added and the reaction mixture was stirred at 80° C. for 2.5 hours. Once cooled to room temperature, saturated sodium thiosulfate solution (50 mL) was added. After stirring for 5 minutes, the mixture was poured into dichloromethane and washed with a 1:1 mixture of 10% aq. sodium thiosulfate and aq. sodium bicarbonate (saturated solution) then washed with a saturated solution of sodium chloride. The solution was dried over magnesium sulfate, filtered, and concentrated under vacuum. The resulting crude product was purified by silica gel chromatography

[ethyl acetate/hexanes (1:1) to 100% ethyl acetate]. The unreacted starting material (0.460 g) was recovered and the title compound was isolated as an off white solid (0.650 g, 46% yield). MS (M+Na) 326.2. 1H NMR (DMSO-d6) δ 10.7 (s, 1H), 8.48 (d, 1H, J=0.016), 8.19 (d, 1H, J=0.015), 7.84 (t, 1H), 5.30 (dd, 1H), 4.96 (m, 2H), 3.11 (m, 1H), 2.60 (m, 1H), 2.42 (m, 1H), 2.14 (m, 1H), 2.03 (m, 1H), 1.87 (m, 1H).

(3S)-3-[(2S)-2-Isoindolinoyl]-2,7-azepinedione (Compound 26)

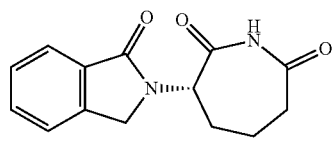 [SMILES: O=C1CCC[C@H](N2Cc3ccccc3C2=O)C(=O)N1]

The title compound was afforded as a white solid (0.015 g, 15% yield) using the methods described above. MS (M+23) 281.3. 1H NMR (DMSO-d6) δ 10.7 (s, 1H), 7.49-7.73 (m, 4H), 5.25 (m, 1H), 4.53 (s, 2H), 3.08 (m, 1H), 2.59 (m, 1H), 2.27 (m, 1H), 2.13 (m, 1H), 2.10 (m, 1H) 1.83 (m, 1H)

(3S)-3-[(2S)-5-Nitro-2-isoindolinoyl]-2,7-azepinedione (Compound 27)

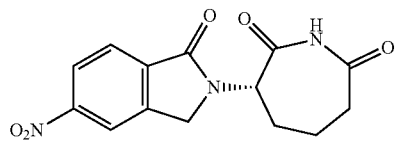 [SMILES: O=C1CCC[C@H](N2Cc3cc([N+](=O)[O-])ccc3C2=O)C(=O)N1]

The title compound was afforded as a white solid (0.037 g, 35% yield) using the methods described above. MS (M+23) 326.1. ¹H NMR (DMSO-d6) δ 10.7 (s, 1H), 7.96-8.54 (m, 3H), 5.25 (m, 1H), 4.66 (s, 2H), 3.10 (m, 1H), 2.55 (m, 1H), 2.27 (m, 1H), 2.13 (m, 1H), 2.10 (m, 1H), 1.83 (m, 1H).

(3S)-3-[(2S)-5-Amino-2-isoindolinoyl]-2,7-azepinedione (Compound 28)

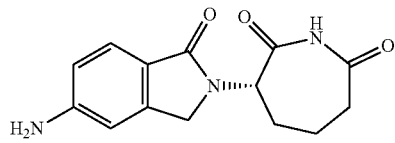

The title compound was afforded as an off white solid (0.007 g, 50% yield) using the methods described above. MS (M+23) 296.2. ¹H NMR (DMSO-d6) δ 10.6 (s, 1H), 7.34 (d, 1H), 6.63 (m, 2H), 5.79 (m, 2H), 5.10 (m, 1H), 4.33 (m, 2H), 3.10 (m, 1H), 2.55 (m, 1H), 2.27 (m, 1H), 2.13 (m, 1H), 2.10 (m, 1H), 1.83 (m, 1H).

(3S)-3-[(2S)-4-Amino-2-isoindolinoyl]-2,7-azepinedione (Compound 30)

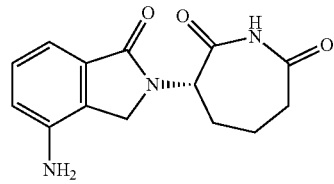 [SMILES: Nc1cccc2c1CN([C@H]1CCCC(=O)NC1=O)C2=O]

The title compound was afforded as an off white solid (0.100 g, 83% yield) using the methods described above. MS (M+23) 296.2. ¹H NMR (DMSO-d6) δ 10.69 (s, 1H), 7.17 (m, 1H), 6.90 (m, 2H), 6.80 (m, 2H), 5.42 (s, 2H), 5.22 (m, 1H), 4.32 (m, 2H), 3.10 (m, 1H), 2.55 (m, 1H), 2.27 (m, 1H), 2.13 (m, 1H), 2.10 (m, 1H), 1.83 (m, 1H).

(3S)-3-[(2S)-4-Methyl-2-isoindolinoyl]-2,7-azepinedione (Compound 31)

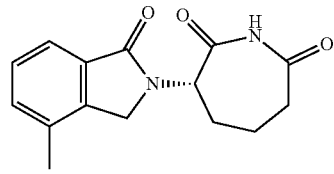 [SMILES: Cc1cccc2c1CN([C@H]1CCCC(=O)NC1=O)C2=O]

The title compound was afforded as a white solid (0.044 g, 15% yield) using the methods described above. MS (M+23) 295.2. ¹H NMR (DMSO-d6) δ 10.7 (s, 1H), 7.55 (m, 1H), 7.42 (m, 2H), 5.25 (m, 1H), 4.48 (s, 2H), 3.08 (m, 1H), 2.61 (m, 1H), 2.34 (s, 3H), 2.27 (m, 1H), 2.13 (m, 1H), 2.03 (m, 1H), 1.85 (m, 1H).

(3S)-3-[(2S)-4-Methyl-2-isoindolinoyl]-2-azepinone (Compound 32)

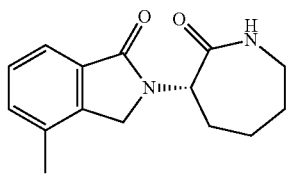 [SMILES: Cc1cccc2c1CN([C@H]1CCCCNC1=O)C2=O]

The title compound was afforded as an off white solid (0.368 g, 30% yield) using the methods described above. MS (M+23) 281.4. ¹H NMR (DMSO-d6) δ 7.80 (t, 1H), 7.51 (m, 1H), 7.39 (m, 2H), 4.92 (d, 1H), 4.50 (q, 2H), 3.23 (m, 1H), 3.08 (m, 1H), 2.33 (s, 3H), 2.00 (m, 2H), 1.85 (m, 2H), 1.75 (m, 1H), 1.30 (m, 1H).

(3S)-3-[(2S)-4-Chloro-2-isoindolinoyl]-2,7-azepinedione (Compound 33)

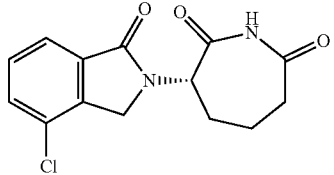 [SMILES: O=C1CCC[C@H](N2Cc3c(Cl)cccc3C2=O)C(=O)N1]

The title compound was afforded as a white solid (0.020 g, 12% yield) using the methods described above. MS (M+23) 315.6. $^1$H NMR (DMSO-d6) δ 10.7 (s, 1H), 7.74 (m, 2H), 7.57 (t, 1H), 5.27 (m, 1H), 4.53 (d, 2H), 3.08 (m, 1H), 2.60 (m, 1H), 2.35 (m, 1H), 2.14 (m, 1H), 2.03 (m, 1H), 1.84 (m, 1H).

(3S)-3-[(2S)-4-Methoxy-2-isoindolinoyl]-2,7-azepinedione (Compound 34)

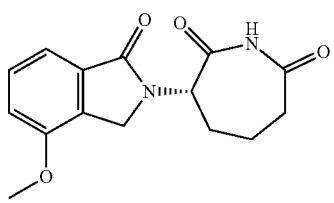 [SMILES: COc1cccc2c1CN([C@H]1CCCC(=O)NC1=O)C2=O]

The title compound was afforded as an off white solid (0.030 g, 18% yield) using the methods described above. MS (M+1) 289.2. $^1$H NMR (DMSO-d6) δ 10.7 (s, 1H), 7.49 (t, 1H), 7.31 (d, 1H), 7.24 (d, 1H), 5.22 (m, 1H), 4.43 (s, 2H), 3.88 (s, 3H), 3.07 (m, 1H), 2.61 (m, 1H), 2.31 (m, 1H), 2.13 (m, 1H), 2.03 (m, 1H), 1.85 (m, 1H).

(3S)-3-[(2S)-5-Methyl-2-isoindolinoyl]-2,7-azepinedione (Compound 35)

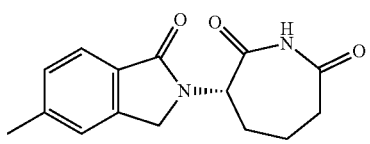 [SMILES: Cc1ccc2c(c1)CN([C@H]1CCCC(=O)NC1=O)C2=O]

The title compound was afforded as an off white solid (0.051 g, 21% yield) using the methods described above. MS (M+1) 295.2. $^1$H NMR (DMSO-d6) δ 10.68 (s, 1H), 7.60 (d, 2H, J=0.015), 7.42 (s, 1H), 7.32 (d, 1H, J=0.014), 5.20 (m, 1H), 4.48 (m, 2H), 3.07 (m, 1H), 2.56 (m, 1H), 2.49 (s, 3H), 2.27 (m, 1H), 2.10 (m, 1H), 2.02 (m, 1H), 1.82 (m, 1H)

(3S)-3-[(2S)-7-Methyl-2-isoindolinoyl]-2,7-azepinedione (Compound 36)

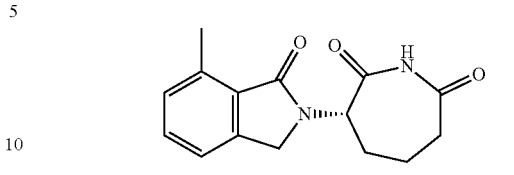

The title compound was afforded as an off white solid (0.025 g, 12% yield) using the methods described above. MS (M+1) 295.3. $^1$H NMR (DMSO-d6) δ 10.7 (s, 1H), 7.48 (t, 1H), 7.41 (d, 1H), 7.25 (d, 1H), 5.20 (m, 1H), 4.47 (q, 2H), 3.06 (m, 1H), 2.61 (s, 3H), 2.57 (m, 1H), 2.24 (m, 1H), 1.98-2.09 (m, 2H), 1.82 (m, 1H).

Pharmaceutical Compositions

Parenteral Pharmaceutical Composition

To prepare a parenteral pharmaceutical composition suitable for administration by injection (subcutaneous, intravenous, or the like), 0.1 mg to 100 mg of a water-soluble salt/soluble material itself/solubilized complex of a compound of a preferred embodiment is dissolved in sterile water and then mixed with 10 mL of 0.9% sterile saline. The mixture is incorporated into a dosage unit form suitable for administration by injection.

Injectable Pharmaceutical Composition

To prepare an injectable formulation, 0.1 mg to 100 mg of a compound of Formula I, 2.0 mL of sodium acetate buffer solution (0.4 M), HCl (1 N) or NaOH (1 M) (q.s. to suitable pH), water (distilled, sterile) (q.s. to 20 mL) are mixed. All of the above ingredients, except water, are combined and stirred and if necessary, with slight heating if necessary. A sufficient quantity of water is then added.

Oral Pharmaceutical Composition

To prepare a pharmaceutical composition for oral delivery, 0.1 mg to 100 mg of a compound of a preferred embodiment is mixed with 750 mg of starch. The mixture is incorporated into an oral dosage unit, such as a hard gelatin capsule, or 0.1 mg to 100 mg of compound is granulated with binder solution such as starch solution along with suitable diluents such as microcrystalline cellulose or like, disintegrants such as croscarmellose sodium, dry the resultant mixture and add lubricant and compress into tablet which is suitable for oral administration.

Sublingual (Hard Lozenge) Pharmaceutical Composition

To prepare a pharmaceutical composition for buccal delivery, such as a hard lozenge, 0.1 mg to 100 mg of a compound of a preferred embodiment is mixed with 420 mg of powdered sugar/mannitol/xylitol or such sugars that provide negative heat of solution to the system, 1.6 mL of light corn syrup, 2.4 mL distilled water, and 0.42 mL mint extract or other flavorants. The mixture is blended and poured into a mold to form a lozenge suitable for buccal administration.

Fast-Disintegrating Sublingual Tablet

A fast-disintegrating sublingual tablet is prepared by mixing 48.5% by weigh of a compound of a preferred embodiment, 20% by weight of microcrystalline cellulose (KG-802), 24.5% by weight of either mannitol or modified dextrose or combination that help dissolve the compressed tablet faster in the mouth, 5% by weight of low-substituted hydroxypropyl cellulose (50 μm), and 2% by weight of magnesium stearate. Tablets are prepared by direct compression (AAPS PharmSciTech. 2006; 7(2):E41). The total weight of the compressed tablets is maintained at 150 mg.

The formulation is prepared by mixing the amount of the compound of a preferred embodiment with the total quantity of microcrystalline cellulose (MCC) and mannitol/modified dextrose or combination, and two-thirds of the quantity of low-substituted hydroxypropyl cellulose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Inhalation Pharmaceutical Composition

To prepare a pharmaceutical composition for inhalation delivery, 0.1 mg to 100 mg of a compound of a preferred embodiment is mixed with 50 mg of anhydrous citric acid and 100 mL of 0.9% sodium chloride solution. The mixture is incorporated into an inhalation delivery unit, such as a nebulizer, which is suitable for inhalation administration, Nebulizer Suspension Pharmaceutical Composition In another embodiment, a compound of a preferred embodiment (0.1 mg to 100 mg) is suspended in sterile water (100 mL); Span 85 (1 g) is added followed by addition of dextrose (5.5 g) and ascorbic acid (10 mg). Benzalkonium chloride (3 mL of a 1:750 aqueous solution) is added and the pH is adjusted to 7 with phosphate buffer. The suspension is packaged in sterile nebulizers.

Transdermal Patch Pharmaceutical Composition

To prepare a pharmaceutical composition for transdermal delivery, 0.1 mg to 100 mg of a compound of a preferred embodiment is embedded in, or deposited on, a patch with a single adhesive face. The resulting patch is then attached to the skin via the adhesive face for transdermal administration.

Topical Gel Pharmaceutical Composition

To prepare a pharmaceutical topical gel composition, 01 mg to 100 mg of a compound of a preferred embodiment is mixed with 1.75 g of hydroxypropyl cellulose, 10 mL of propylene glycol, 10 mL of isopropyl myristate and 100 mL, of purified alcohol USP. The resulting gel mixture is then incorporated into containers, such as tubes, which are suitable for topical administration.

Ophthalmic Solution

To prepare a pharmaceutical ophthalmic solution composition, 0.1 mg to 100 mg of a compound of a preferred embodiment is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 0.1 mg to 100 mg of a compound of a preferred embodiment is mixed with 30 mL of a 0.05M phosphate buffer solution (pH 4.4). The solution is placed in a nasal administrator designed to deliver 100 μl of spray for each application.

Cell-Based Assays

Western Blot Protocol: K562, U266, and Jurkat cell lines were grown in RPMI 1640 supplemented with streptomycin, penicillin and 10% fetal bovine serum.

Cells were cultured at approximately $10^6$ cells per ml, DMSO or the indicated compound was added to the cells and allowed to incubate for the indicated period. Whole cell extract was prepared with M-Per Reagent according to manufacturer's protocol (Pierce). Briefly, ~5×$10^6$ cells were washed once in PBS, the cell pellet was resuspended in M-PER solution and allowed to incubate for 10 min at room temperature. Cell debris was removed by centrifugation and the cleared whole cell lysate was transferred to a new tube for further analysis.

For western blot analysis, whole cell extracts were separated on 4-12% SDS-polyacrylamide gels, transferred to nitrocellulose and probed with the indicated primary antibodies. Membranes were subsequently washed and probed with the appropriate horseradish peroxidase (HRP)-conjugated secondary antibody. The signal was detected using the WesternBright Sirius Reagent (Advansta).

The following antibodies were used in these studies:

Cereblon rabbit polyclonal antibody: Applied Biologicals Material Inc, # Y055422

I2PP2A mouse monoclonal antibody: Santa Cruz Biotechnology, sc-133138.

Casein kinase 1 alpha goat polyclonal antibody: Santa Cruz Biotechnology, sc-6477.

Casein kinase 1 epsilon goat polyclonal antibody: Santa Cruz Biotechnology, sc-6471

Ikaros rabbit monoclonal antibody: Cell Signaling, #9034, D10E5

Aiolos rabbit polyclonal antibody: Cell Signaling, #12720

Donkey anti-goat IgG-HRP: Santa Cruz Biotechnology, sc-2056

Goat anti-rabbit IgG-HRP: Cell Signaling, #7074

Goat anti-mouse IgG-HRP: Sigma, A4416

PBMCs induced with LPS: Frozen primary blood mononuclear cells (PBMCs) were purchased from AllCells. Cells were quick thawed, washed 1-time with RPMI-1640/10% FBS/1% Penicillin/1% Streptomycin and plated in 96 well plates at 200,000 cells per well. Cells were pretreated with DMSO only, Pomalidomide (Pom), lenalidomide (Len) or the indicated compounds for 1 hour and then induced with 100 ng/ml lipopolysaccharide (LPS) or 250 ng/ml LPS as indicated for 18-24 hours. The supernatant was analyzed for IL-1 beta, IL-6 and TNF alpha using Meso Scale assay according to manufacturer's protocol. The negative control wells were treated with DMSO. Compound activity is measured as a percentage of the DMSO control.

PBMCs: AllCells PB003F, Normal Peripheral Blood MNC

Media: RPMI 1640/10% FBS/1% Pen-Strep

Assay kit: Meso Scale Discovery 4-Plex ProInflam II (IL-1b, IL-6, IL-8, TNFα), K15053D-2

Compound A:

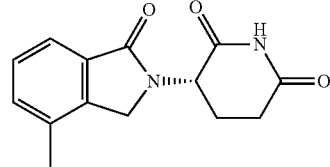 [SMILES: Cc1cccc2c1CN([C@H]1CCC(=O)NC1=O)C2=O]

PBMCs induced with Anti-CD3 Antibody: 96-well plates were precoated with anti-CD3 (OKT-3) antibody by overnight incubation with anti-CD3 antibody at 1 ug per ml in PBS. PBMCs were prepared as described above and subsequently plated into the anti-CD3 coated 96-well plates at 300,000 to 750,000 cells per well, followed by the addition of DMSO only, pomalidomide, lenalidomide or the indicated Compounds. After 72 hours, supernatant was analyzed using the IL-2 Meso Scale assay according to manufacturer's protocol. The negative control wells were treated with DMSO. Compound activity is measured as a percentage of the DMSO control.

PBMCs: AllCells PB003F, Normal Peripheral Blood MNC

Media: RPMI 1640/10% FBS/1% Pen-Strep

Anti-CD3 antibody: eBioscience 16-0037-85, 1 mg/ml

Assay kit: Meso Scale Discovery Il2 Single Plex—K151QQD-2

For examples using primary blood mononuclear cells (PBMCs), frozen PBMCs were purchased from AllCells. Cells were thawed in RPMI overnight and plated in 96 well plates at 100,000-200,000 cells per well. Cells were pretreated with compounds for 1 hour and then induced with 200 uM lipopolysaccharide (LPS) for 18-24 hours. Cytokines in the media were measured according to MesoScale protocol. Pom-10 is 10 uM pomalidomide; Thal-30 is 30 uM thalidomide. The negative control wells were treated with DMSO. Compound activity is measured as a percentage of LPS-induced activity.

Figure 2:
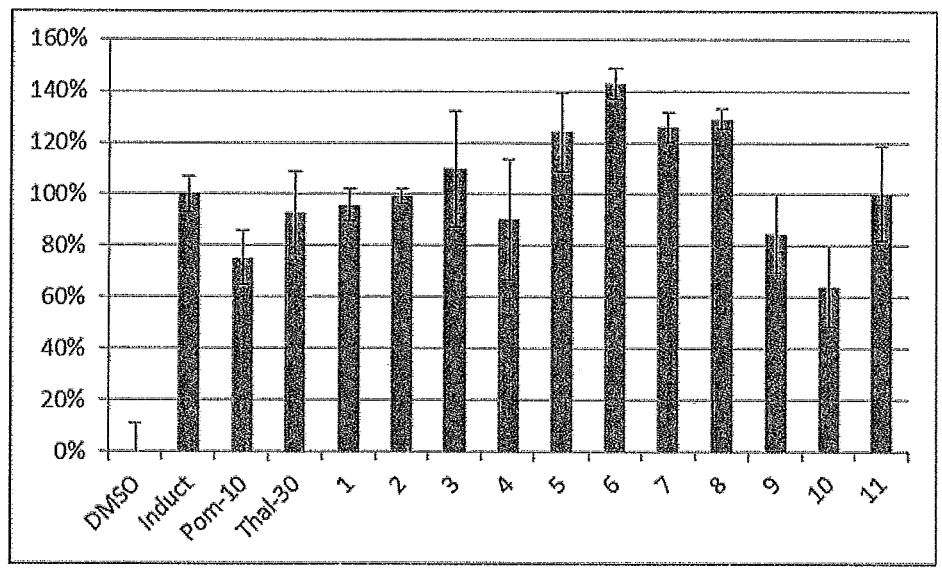
FIG. 2 represents the activity against IL-6 in CD14 macrophages, plated in 96 well plates and treated with 100 ng/mL macrophage colony-stimulating factor (M-CSF) for up to 1 week to differentiate cells into macrophages. Cells were pretreated with compounds for 1 hour and then induced with either 200 ng/ml LPS or 20 ng/ml of TNF-alpha for 18-24 hours. Cytokines in the media were measured according to MesoScale protocol. Pom-10 is 10 uM pomalidomide; Thal-30 is 30 uM thalidomide. The negative control wells were treated with DMSO. Cells were treated with the indicated Compound (20 uM). Compound activity is measured as a percentage of LPS-induced activity.
Figure 3:
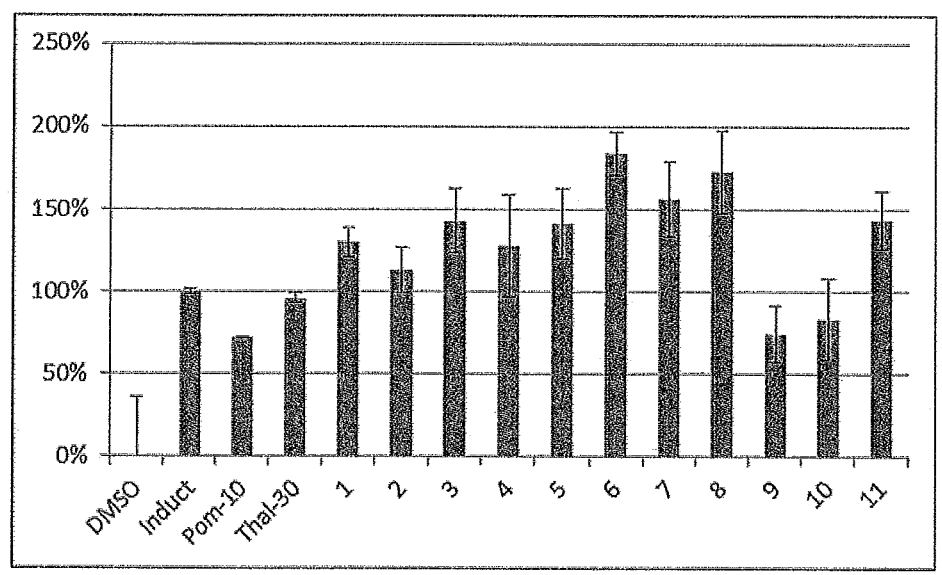
FIG. 3 represents the activity against TNF-alpha in CD14 macrophages, plated in 96 well plates and treated with 100 ng/mL macrophage colony-stimulating factor (M-CSF) for up to 1 week to differentiate cells into macrophages. Cells were pretreated with compounds for 1 hour and then induced with either 200 ng/ml LPS for 18-24 hours. Cytokines in the media were measured according to MesoScale protocol. Pom-10 is 10 uM pomalidomide; Thal-30 is 30 uM thalidomide. The negative control wells were treated with DMSO. Cells were treated with the indicated compound (20 uM), Compound activity is measured as a percentage of LPS-induced activity.
Figure 4:
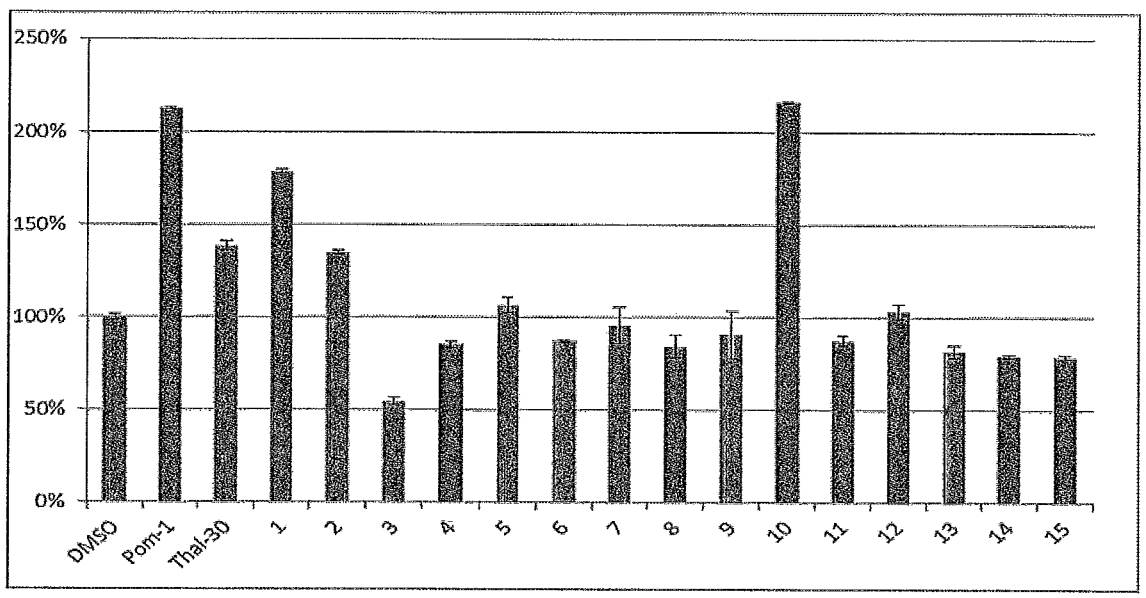
FIG. 4 represents Anti-CD3-induced IL-2 secretion in PBMCs. 1 ug/ml anti-CD3 (OKT-3) antibody in PBS coated onto 96-well plates overnight at 4° C. 150,000 PBMCs were added to each well, followed by addition of DMSO only, pomalidomide (1 uM), thalidomide (30 uM), or Compounds 1-15 (20 uM). Induction was measured after 48 hours.

For examples using CD14 macrophages, frozen CD14+ mobilized peripheral blood monocytes were purchased from AllCells. Cells were plated in 96 well plates and treated with 100 uM macrophage colony-stimulating factor (M-CSF) for up to 1 week to differentiate cells into macrophages. Cells were pretreated with compounds for 1 hour and then induced with either 200 uM LPS or 20 uM of TNF-alpha for 18-24 hours. Cytokines in the media were measured according to MesoScale protocol. Pom-10 is 10 uM pomalidomide; Thal-30 is 30 uM thalidomide. The negative control wells were treated with DMSO. Compound activity is measured as a percentage of LPS-induced activity. IL-1-beta activity is shown in FIG. 1; IL-6 activity is shown in FIG. 2; and TNF-alpha activity is shown in FIG. 3.

Figure 5:
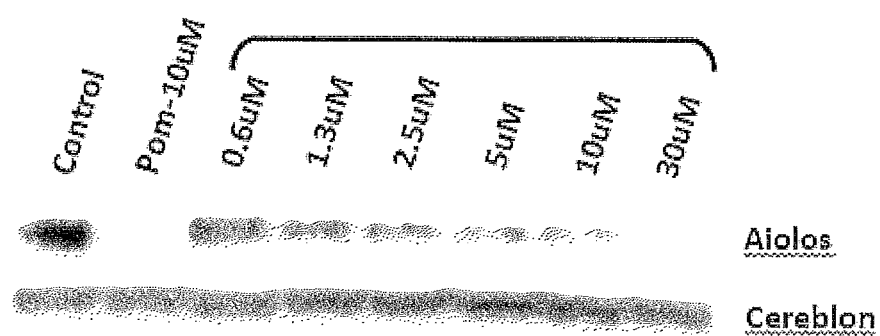
FIG. 5 represents a Western Blot from U266 cells treated with Control (DMSO only), pomalidomide, or Compound 10 at the indicated concentration for 4 hrs. Cells were lysed using MPER (Pierce) and a Western Blot was performed using anti-aiolos and anti-cereblon antibodies.
Figure 6:
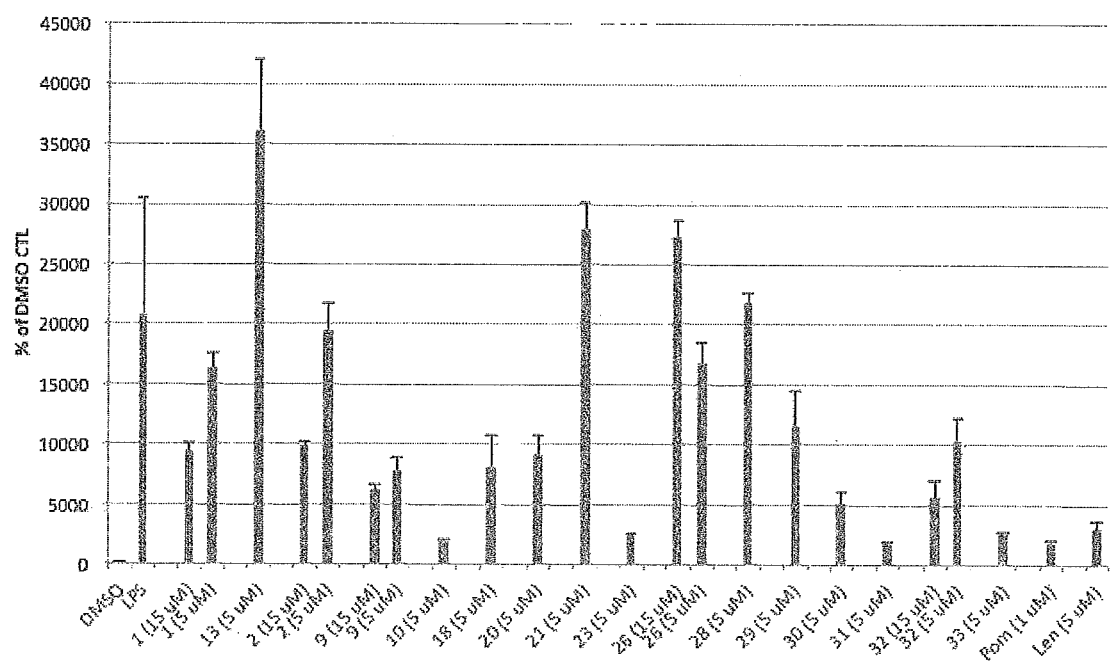
FIG. 6 represents IL-1-beta activity in human PBMCs stimulated with LPS (100 ng/mL), 18 hours after dosing with Controls (DMSO or LPS only), Compound A, pomalidomide, lenalidomide, or one of Compounds 1, 2, 9, 10, 13, 18, 20, 21, 23, 26, 28, 29, 30, 31, 32, or 33.
Figure 7:
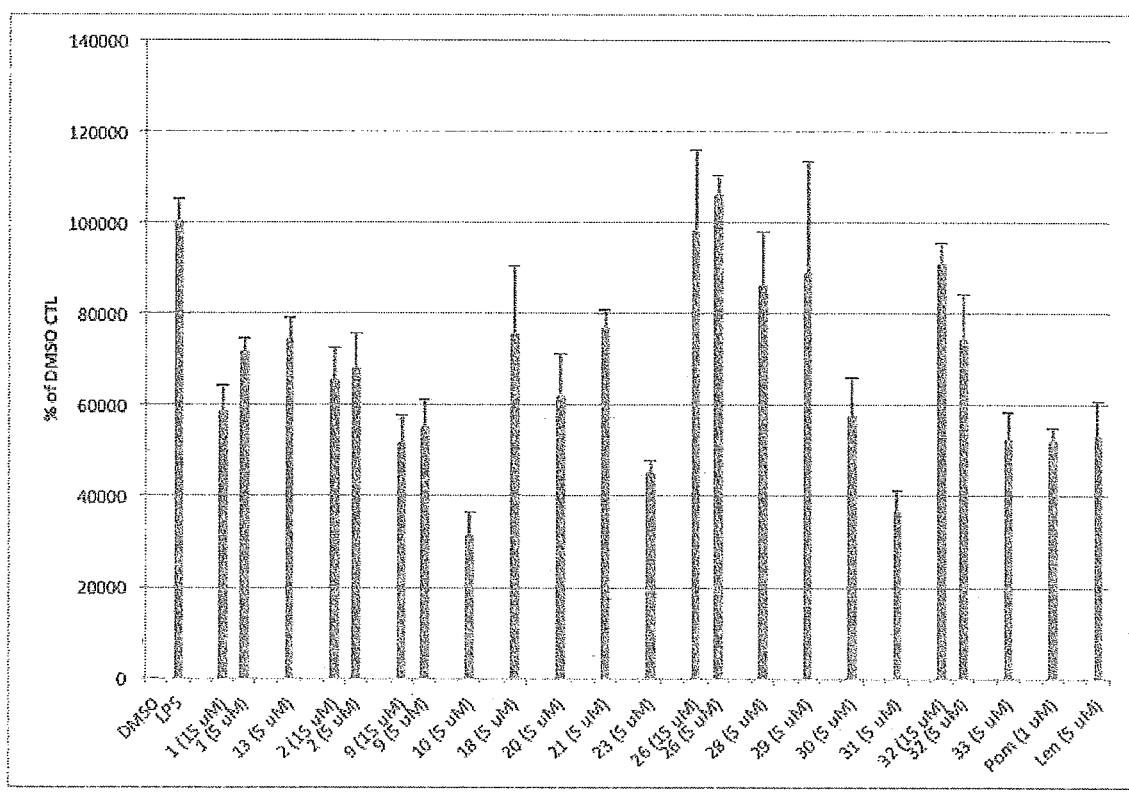
FIG. 7 represents IL-6 activity in human PBMCs stimulated with LPS (100 ng/mL), 18 hours after dosing with Controls (DMSO or LPS only), Compound A, pomalidomide, lenalidomide, or one of Compounds 1, 2, 9, 10, 13, 18, 20, 21, 23, 26, 28, 29, 30, 31, 32, or 33.
Figure 8:
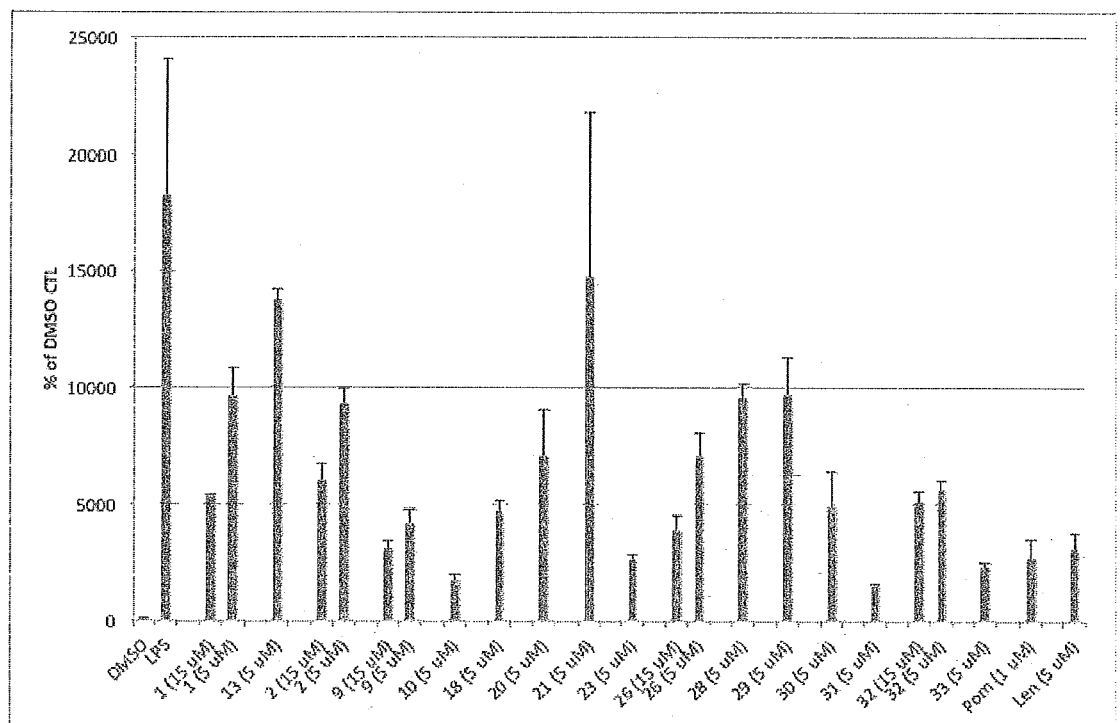
FIG. 8 represents TNF-alpha activity in human PBMCs stimulated with LPS (100 ng/mL), 18 hours after dosing with Controls (DMSO or LPS only), Compound A, lenalidomide, or one of Compounds 1, 2, 9, 10, 13, 18, 20, 21, 23, 26, 28, 29, 30, 31, 32, or 33.
Figure 9:
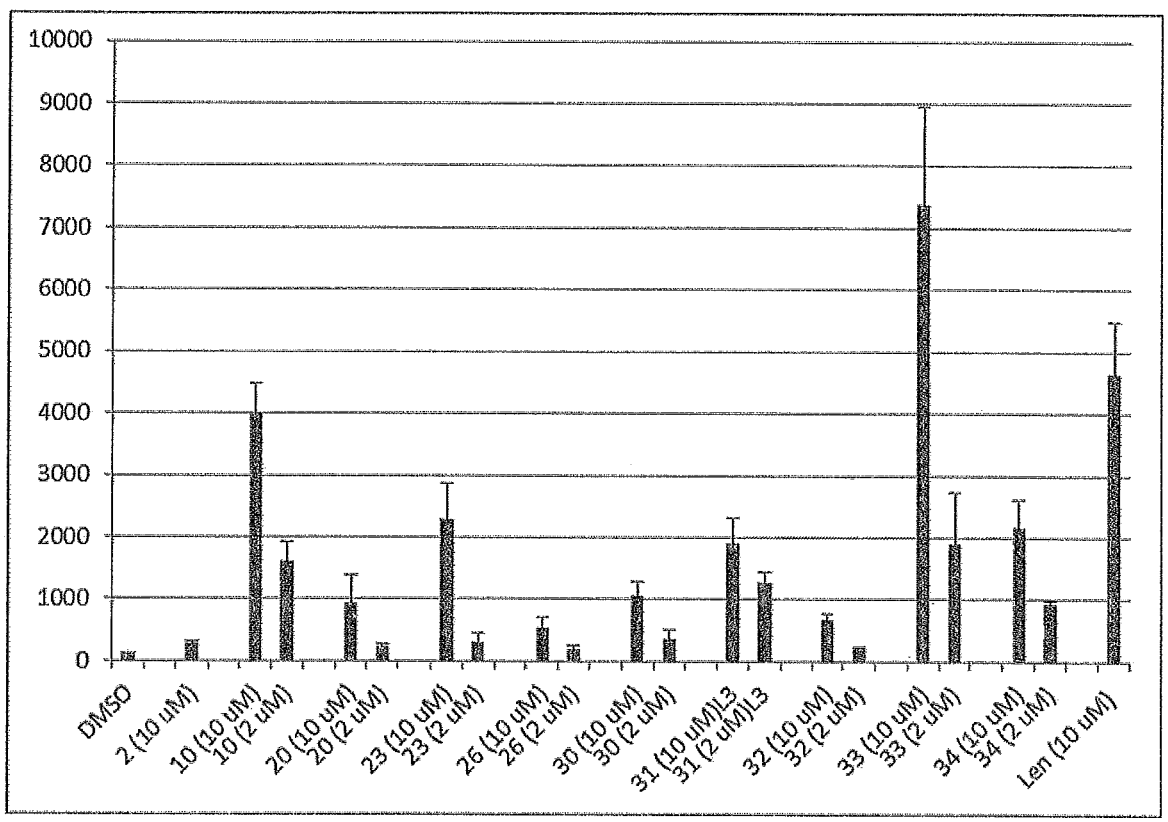
FIG. 9 represents IL-2 expression from anti-CD3-stimulated human PBMCs after treatment (72 hours post-induction) with Control (DMSO only), pomalidomide, lenalidomide, or one of Compounds 2, 10, 20, 23, 26, 30, 31, 32, 33, or 34.
Figure 10:
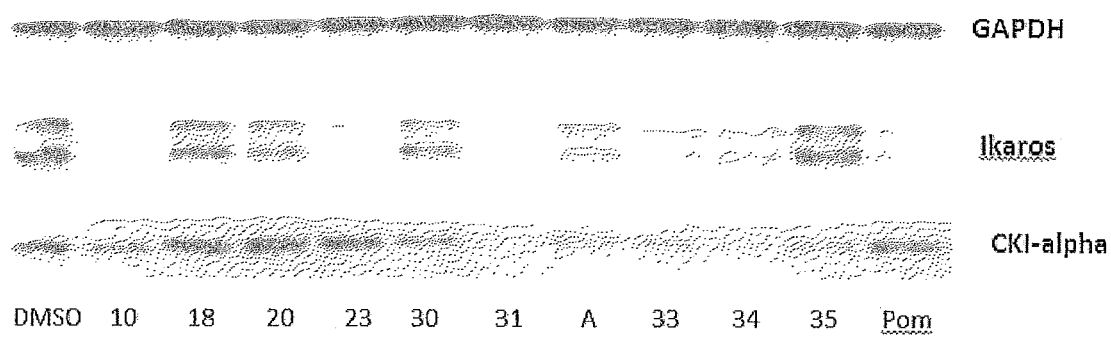
FIG. 10 represents a Western Blot from Jurkat cells treated with Control (DMSO only), Compound A, pomalidomide, or one of Compounds 10, 18, 20, 23, 30, 31, 33, 34, or 35. Cells were lysed using MPER (Pierce) and a Western Blot was performed using anti-ikaros, anti-caseine kinase 1-alpha, and anti-GAPDH antibodies.
Figure 11:
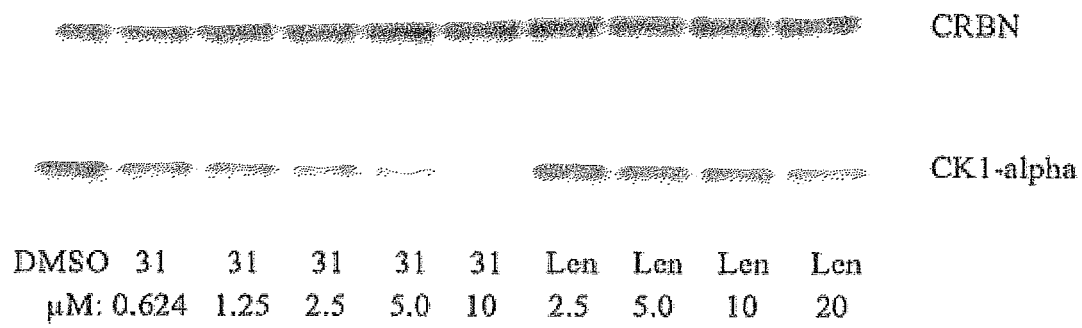
FIG. 11 represents a Western Blot of a dose-response from K562 cells treated with Control (DMSO only), lenalidomide, or Compound 31. Cells were lysed using MPER (Pierce) and a Western Blot was performed using anti-caseine kinase 1-alpha and anti-cereblon antibodies.
Figure 12:
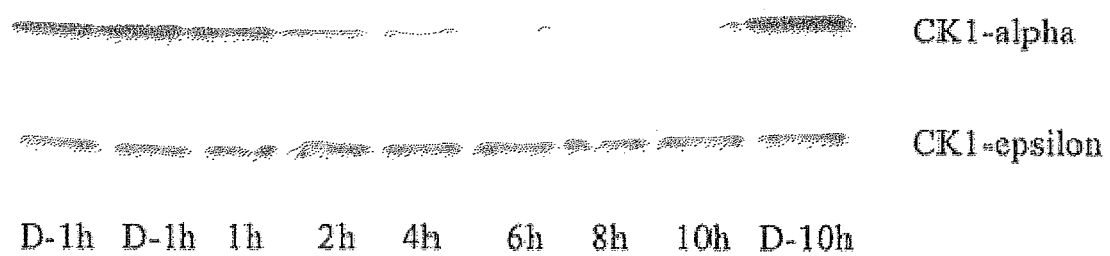
FIG. 12 represents a Western Blot of a time-course from K562 cells treated with Compound 31. Cells were lysed using MPER (Pierce) and a Western Blot was performed using anti-caseine kinase 1-alpha and anti-caseine kinase 1-epsilon.
Figure 13A:
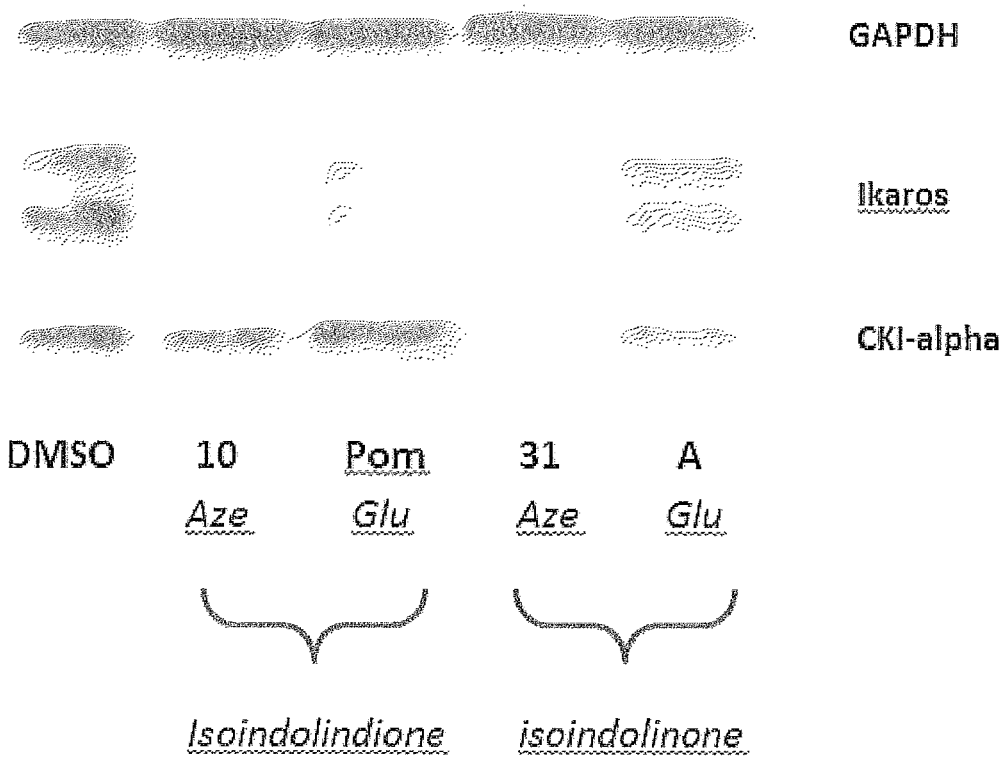
FIG. 13A represents a Western Blot from Jurkat cells treated for 5 hours with Control (DMSO only), Compound A (10 uM), pomalidomide (10 uM), or Compounds 10 and 31 (10 uM). Cells were lysed using M-PER (Pierce) and a Western Blot was performed using anti-Ikaros, anti-casein kinase 1-alpha, and anti-GAPDH antibodies.
Figure 13B:
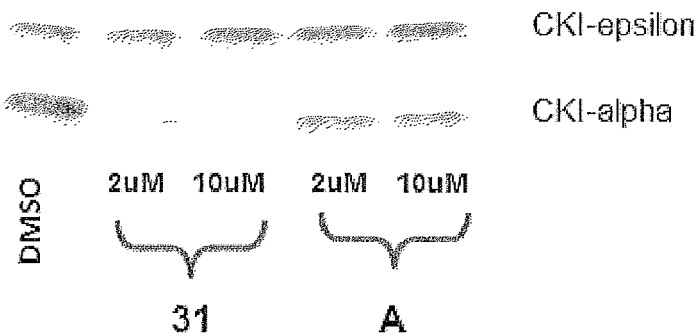
FIG. 13B represents a Western Blot from Jurkat cells treated with Control (DMSO only), Compound A, or Compound 31 for 5 hours at the indicated concentration. Cells were then lysed using M-PER (Pierce) and a Western Blot was performed using anti-casein kinase 1-alpha, and anti-casein kinase 1-epsilon.
Figure 13C:
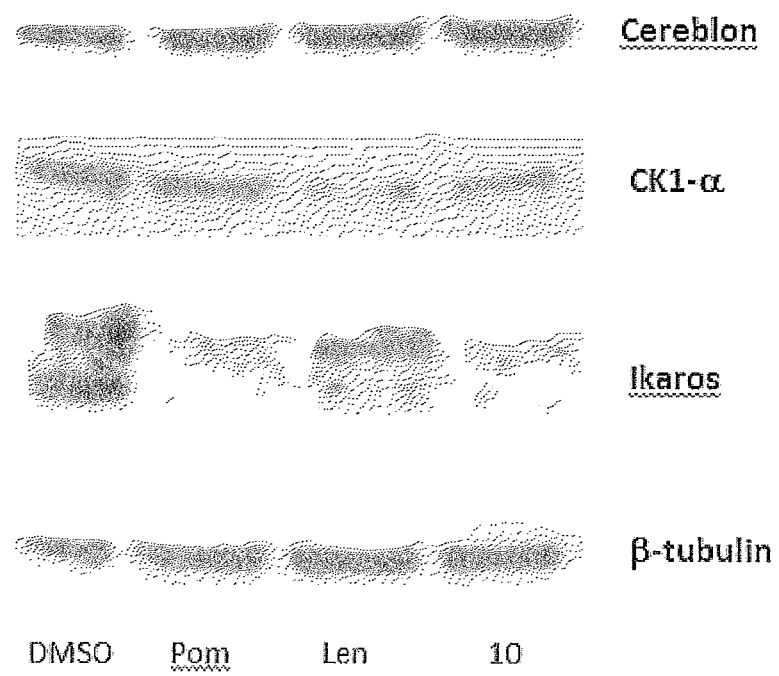
FIG. 13C represents a Western Blot from MM1S cells treated with Control (DMSO only), pomalidomide (Pom), lenalidomide (Len) or Compound 10 at 10 uM for 8 hrs. Cells were then lysed using M-PER (Pierce) and a Western Blot was performed using anti-casein kinase 1, anti-Ikaros, anti-cereblon, and anti-beta-tubulin antibodies.
Figure 14A:
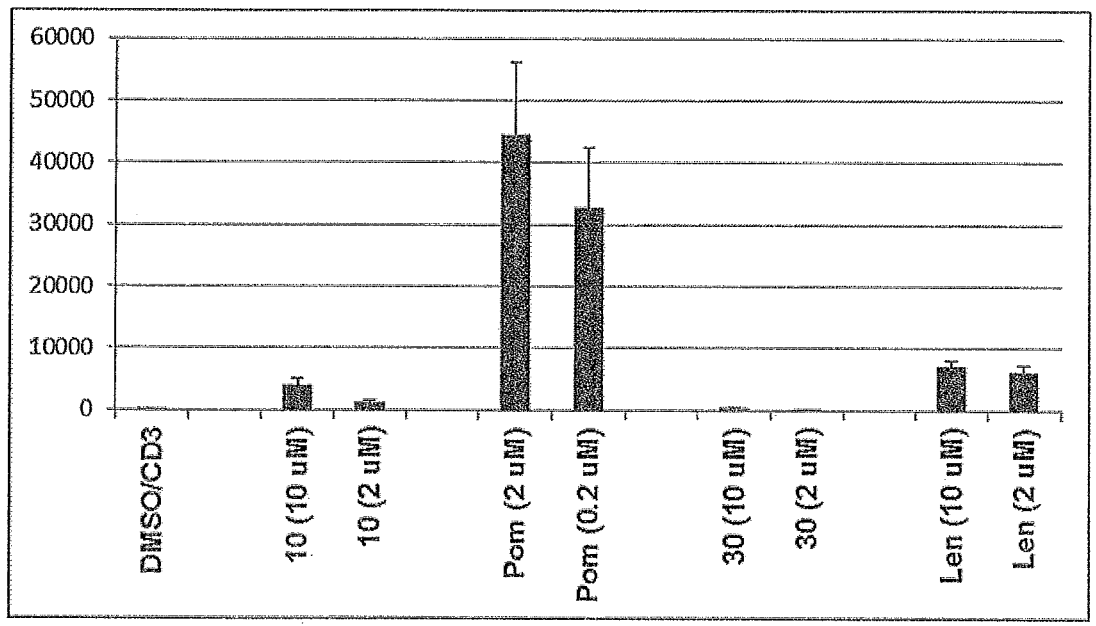
FIG. 14A represents anti-CD3-induced IL-2 secretion in PBMCs. A 96-well plate was coated with anti-CD3 (OKT-3) antibody by overnight incubation with anti-CD3 antibody at 1 ug per ml in PBS. PBMCs (donor 1) were prepared as described above and subsequently plated into the anti-CD3 antibody coated 96-well plate at 300,000 to 750,000 cells per well, followed by the addition of DMSO only, pomalidomide (Pom), lenalidomide (len), Compounds 10 or Compound 30 at the indicated concentration. After 72 hours, supernatant was analyzed using the IL-2 Meso Scale assay according to manufacturer's protocol. The negative control wells were treated with DMSO. Compound activity is measured as a percentage of the DMSO control.
Figure 14B:
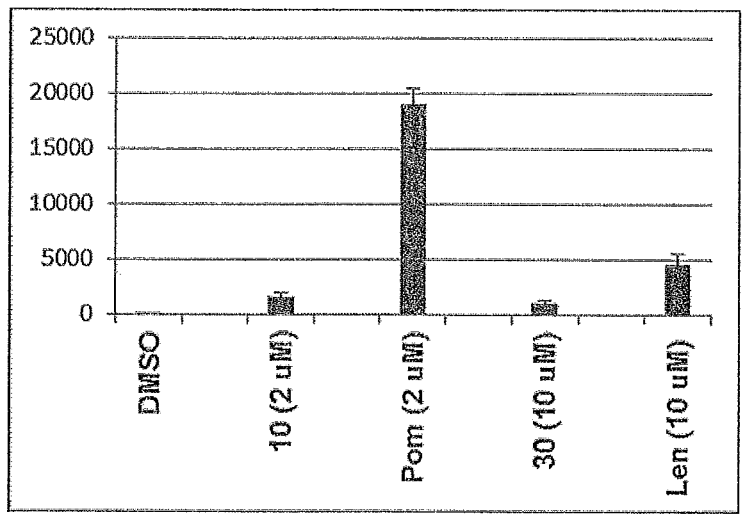
FIG. 14B represents anti-CD3-induced IL-2 secretion in PBMCs. A 96-well plate was coated with anti-CD3 (OKT-3) antibody by overnight incubation with anti-CD3 antibody at 1 ug per ml in PBS. PBMCs (donor 2) were prepared as described above and subsequently plated into the anti-CD3 antibody coated-96-well plate at 300,000 to 750,000 cells per well, followed by the addition of DMSO only, pomalidomide (Pom), lenalidomide (len), Compounds 10 or Compound 30 at the indicated concentration. After 72 hours, supernatant was analyzed using the IL-2 Meso Scale assay according to manufacturer's protocol. The negative control wells were treated with DMSO. Compound activity is measured as a percentage of the DMSO control.
Figure 14C:
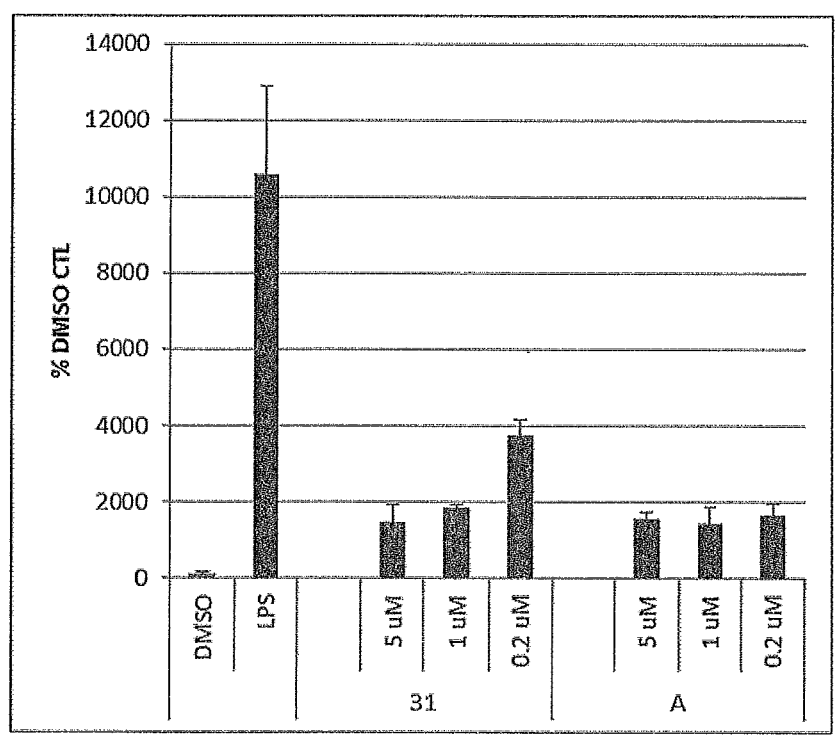
FIG. 14C represents TNF alpha activity in human PBMCs stimulated with LPS (100 ng/mL), 18 hours after dosing with Controls (DMSO or LPS only), Compound A or Compound 31 at the indicated concentration.
Figure 14D:
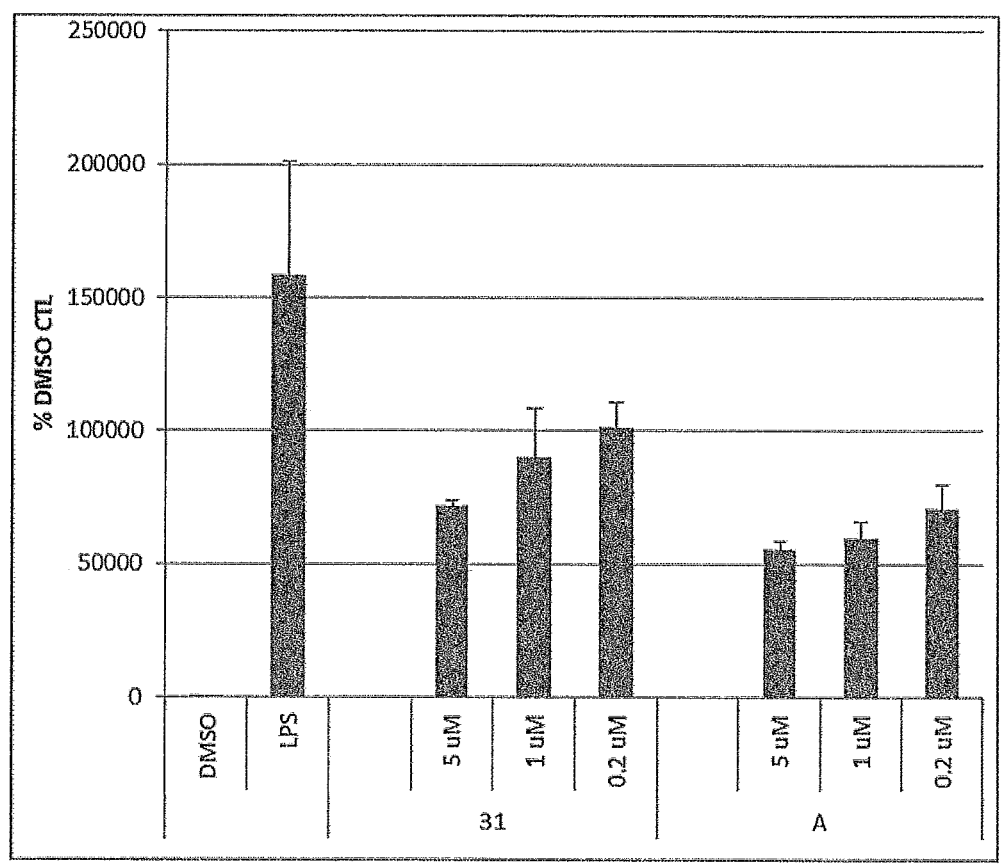
FIG. 14D represents IL-6 activity in human PBMCs stimulated with LPS (100 ng/mL), 18 hours after dosing with Controls (DMSO or LPS only), Compound A or Compound 31 at the indicated concentration.
Figure 14E:
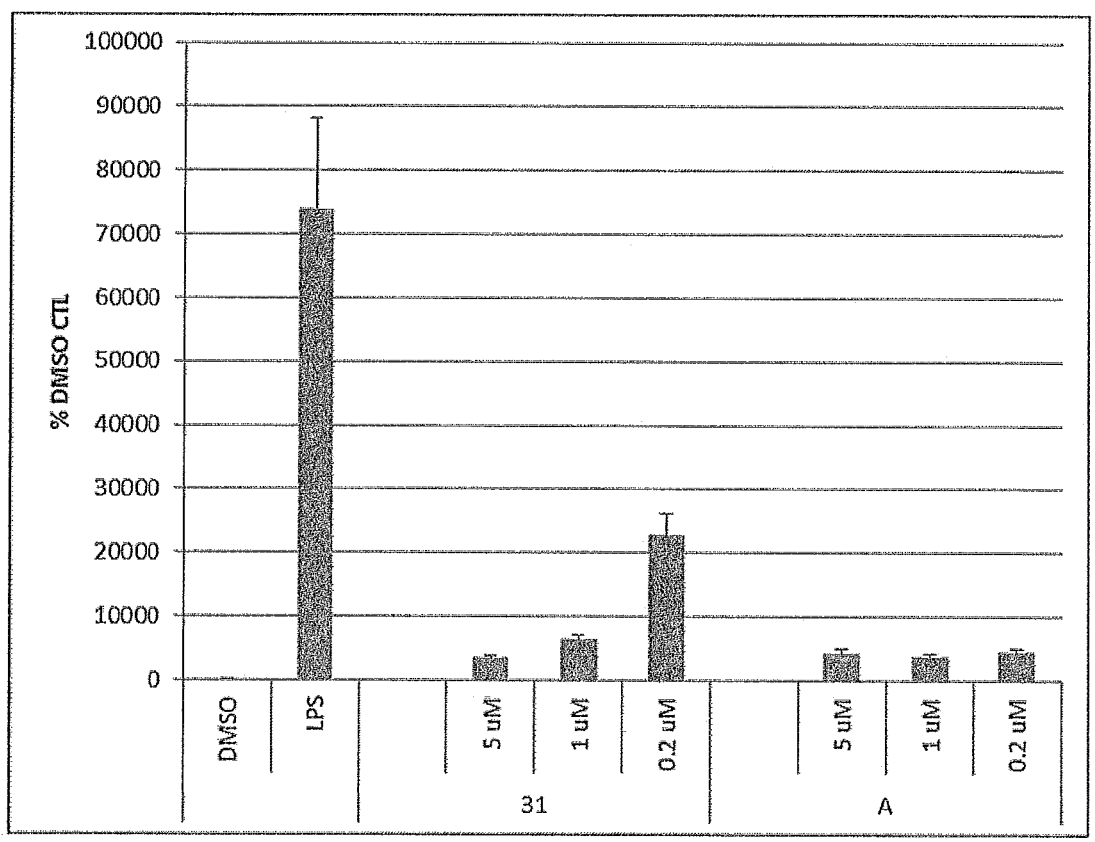
FIG. 14E represents IL-1-beta activity in human PBMCs stimulated with LPS (100 ng/mL), 18 hours after dosing with Controls (DMSO or LPS only), Compound A or Compound 31 at the indicated concentration.

Anti-CD3-IL-2 Induction 1 ug/ml anti-CD3 (OKT-3) antibody in PBS coated onto 96-well plates overnight at 4° C. 150,000 PBMCs were added to each well, following by addition of DMSO only, pomalidomide (Pom), thalidomide (Thal), or Compounds 1-15 (as described above). After 48 hrs, supernatant was analyzed using the IL-2 mesoscale assay according to manufacturer's protocol. Anti-CD3-IL-2 activity is shown in FIG. 5.

Aiolos Western Blot

U266 cells were treated with Control (DMSO only), pomalidomide, or Compound 10 for 4 hrs. Cells were lysed using MPER (Pierce) and a Western blot was performed using anti-aiolos and anti-cereblon antibodies in standard Western Blot protocols (See FIG. 5).

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of inhibiting the activity of a protein, comprising contacting a cell with a compound of Formula (I):

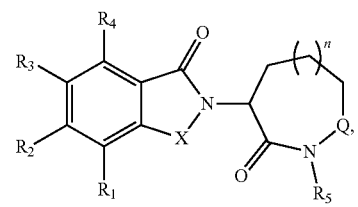

or a pharmaceutically acceptable salt thereof, wherein:
the protein is selected from the group consisting of IL-1β, IL-6, TNF-α, CK1-α, aiolos, and ikaros;
$R_1$ is selected from the group consisting of halogen, cyano, nitro, optionally substituted amino, optionally substituted $C_1$ to $C_6$ alkoxy, optionally substituted $C_1$ to $C_6$ alkyl, optionally substituted $C_3$ to $C_8$ carbocyclyl, optionally substituted $C_6$ to $C_{10}$ aryl, optionally substituted 3-10 membered heterocyclyl, and optionally substituted 5-10 membered heteroaryl;
$R_2$, $R_3$, and $R_4$ are each independently selected from the group consisting of H, deuterium, halogen, cyano, nitro, optionally substituted amino, optionally substituted C-amido, optionally substituted N-amido, optionally substituted —C(═O)OR, optionally substituted sulfonyl, optionally substituted S-sulfonamido, optionally substituted N-sulfonamido, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted 3-10 membered heterocyclyl, and optionally substituted 5-10 membered heteroaryl;
$R_5$ is selected from the group consisting of H, deuterium, and unsubstituted $C_1$ to $C_6$ alkyl;
X is selected from the group consisting of $CH_2$ and C═O;
Q is C═O;
n is 1;
R is $C_1$ to $C_6$ alkyl;
wherein
a 3-10 membered heterocyclyl group is a ring system having between 3 and 10 atoms, including 1 to 3 heteroatoms independently selected from the group consisting of oxygen, nitrogen, and sulfur; and
wherein a 5-10 membered heteroaryl group is a aromatic ring system having between 5 and 10 atoms, including 1 to 3 heteroatoms independently selected from the group consisting of oxygen, nitrogen, and sulfur.

2. The method of claim 1, wherein the method inhibits the activity of IL-1β, IL-6, or TNF-α.

3. The method of claim 1, wherein the method inhibits the activity of CK1-α, aiolos or ikaros.

4. The method of claim 1, wherein $R_5$ is H; $R_1$ is an unsubstituted $C_1$ to $C_6$ alkyl, an unsubstituted $C_1$ to $C_6$ alkoxy, an unsubstituted $C_3$ to $C_8$ carbocyclyl, halogen, nitro, or $NH_2$; $R_2$ is H or D; $R_3$ is H or halogen; and $R_4$ is H or D.

5. The method of claim 1, wherein $R_5$ is H; $R_1$ is an unsubstituted $C_1$ to $C_6$ alkyl, or $NH_2$; $R_2$ is H or D; $R_3$ is H or halogen; and $R_4$ is H or D.

6. The method of claim 1, wherein $R_1$ is an unsubstituted $C_3$ to $C_8$ carbocyclyl or $NH_2$; $R_2$ is H or D; $R_3$ is H or halogen; $R_4$ is H or D; and $R_5$ is H.

7. The method of claim 1, wherein $R_1$ is an unsubstituted $C_3$ to $C_8$ carbocyclyl; $R_2$ is H or D; $R_3$ is H, fluoro, or chloro; $R_4$ is H or D; and $R_5$ is H.

8. The method of claim 1, wherein $R_1$ is an unsubstituted $C_4$ to $C_5$ carbocyclyl; $R_2$ is H; $R_3$ is H, fluoro, or chloro; $R_4$ is H; and $R_5$ is H.

9. The method of claim 1, wherein X is $CH_2$; $R_1$ is an unsubstituted $C_4$ to $C_5$ cycloalkyl; $R_2$ is H; $R_3$ is H, fluoro or chloro; $R_4$ is H; and $R_5$ is H.

10. The method of claim 1, wherein the compound of Formula (I) is selected from the group consisting of

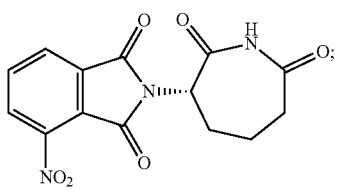

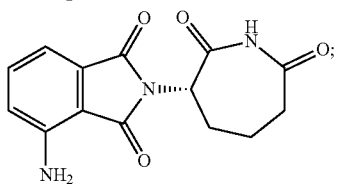

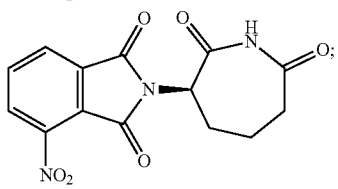

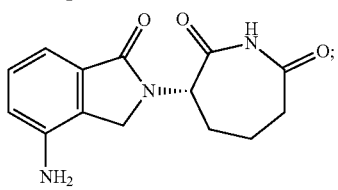

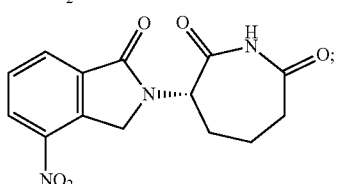

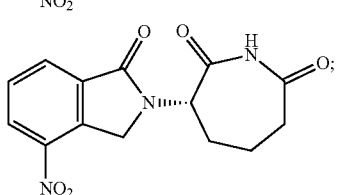

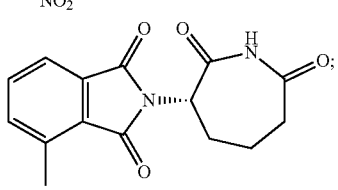

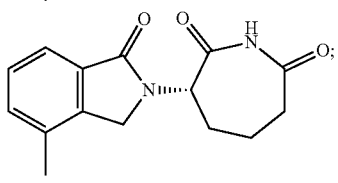

-continued

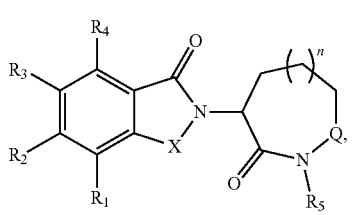

and pharmaceutically acceptable salts of the foregoing.

11. A method of inducing the activity of IL-2, comprising contacting a cell with a compound of Formula (I):

(I)

or a pharmaceutically acceptable salt thereof, wherein:
$R_1$ is selected from the group consisting of halogen, cyano, nitro, optionally substituted amino, optionally substituted $C_1$ to $C_6$ alkoxy, optionally substituted $C_1$ to $C_6$ alkyl, optionally substituted $C_3$ to $C_8$ carbocyclyl, optionally substituted $C_6$ to $C_{10}$ aryl, optionally substituted 3-10 membered heterocyclyl, and optionally substituted 5-10 membered heteroaryl;
$R_2$, $R_3$, and $R_4$ are each independently selected from the group consisting of H, deuterium, halogen, cyano, nitro, optionally substituted amino, optionally substituted C-amido, optionally substituted N-amido, optionally substituted —C(=O)OR, optionally substituted sulfonyl, optionally substituted S-sulfonamido, optionally substituted N-sulfonamido, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted 3-10 membered heterocyclyl, and optionally substituted 5-10 membered heteroaryl;
$R_5$ is selected from the group consisting of H, deuterium, and unsubstituted $C_1$ to $C_6$ alkyl;
X is selected from the group consisting of $CH_2$ and C=O;
Q is C=O;
n is 1;
R is $C_1$ to $C_6$ alkyl;
wherein a 3-10 membered heterocyclyl group is a ring system having between 3 and 10 atoms, including 1 to 3 heteroatoms independently selected from the group consisting of oxygen, nitrogen, and sulfur; and wherein a 5-10 membered heteroaryl group is a aromatic ring system having between 5 and 10 atoms, including 1 to 3 heteroatoms independently selected from the group consisting of oxygen, nitrogen, and sulfur.

12. The method of claim 11, wherein $R_1$ is an unsubstituted $C_1$ to $C_6$ alkyl, an unsubstituted $C_3$ to $C_8$ carbocyclyl, an unsubstituted $C_1$ to $C_6$ alkoxy, nitro, halogen, or $NH_2$; $R_2$ is H or D; $R_3$ is H or halogen; $R_4$ is H or D; and $R_5$ is H.

13. The method of claim 11, wherein $R_1$ is an unsubstituted $C_1$ to $C_6$ alkyl or $NH_2$; $R_2$ is H or D; $R_3$ is H or halogen; $R_4$ is H or D; and $R_5$ is H.

14. The method of claim 11, wherein $R_1$ is an unsubstituted $C_3$ to $C_8$ carbocyclyl; $R_2$ is H or D; $R_3$ is H, fluoro, or chloro; $R_4$ is H or D; and $R_5$ is H.

15. The method of claim 11, wherein X is $CH_2$; $R_1$ is an unsubstituted $C_4$ to $C_5$ cycloalkyl; $R_2$ is H; $R_3$ is H, fluoro or chloro; $R_4$ is H; and $R_5$ is H.

* * * * *